United States Patent
Boettcher et al.

(10) Patent No.: US 10,571,450 B2
(45) Date of Patent: Feb. 25, 2020

(54) MOBILE EXPLOSION LAB SYSTEMS AND METHODS FOR INCENDIVITY TESTING

(71) Applicant: The Boeing Company, Chicago, IL (US)

(72) Inventors: Philipp Andreas Boettcher, Philadelphia, PA (US); Eddie Kwon, Seattle, WA (US); Jason Scott Damazo, Seattle, WA (US)

(73) Assignee: The Boeing Company, Chicago, IL (US)

( * ) Notice: Subject to any disclaimer, the term of this patent is extended or adjusted under 35 U.S.C. 154(b) by 312 days.

(21) Appl. No.: 15/263,789

(22) Filed: Sep. 13, 2016

(65) Prior Publication Data

US 2018/0074036 A1 Mar. 15, 2018

(51) Int. Cl.
*G01N 33/22* (2006.01)
(52) U.S. Cl.
CPC .................................. *G01N 33/227* (2013.01)
(58) Field of Classification Search
CPC ........ B32B 2307/3065; B32B 2605/18; G01N 33/227
See application file for complete search history.

(56) References Cited

U.S. PATENT DOCUMENTS

| | | | | |
|---|---|---|---|---|
| 6,253,777 B1 * | 7/2001 | Anderson | ............... | E04H 15/54 135/115 |
| 7,862,227 B2 * | 1/2011 | West | ............. | G01N 25/22 374/31 |
| 8,171,837 B2 * | 5/2012 | Asahina | .................. | F42D 5/045 86/50 |
| 8,858,222 B1 * | 10/2014 | Adams | ..................... | F23N 5/20 431/1 |
| 2008/0198524 A1 * | 8/2008 | McConnell | ............. | F23D 14/82 361/91.2 |
| 2012/0088050 A1 * | 4/2012 | Lavature | ................ | B32B 5/028 428/41.1 |
| 2014/0331743 A1 * | 11/2014 | Kwon | .................... | G01N 15/10 73/23.31 |

OTHER PUBLICATIONS

Buhler et al., "Test methodology to evaluate the safety of materials using spark incendivity," Journal of Electrostatics, vol. 64, pp. 744-751, 2006.

(Continued)

*Primary Examiner* — Sally A Merkling
(74) *Attorney, Agent, or Firm* — Dascenzo Intellectual Property Law, P.C

(57) ABSTRACT

Methods of incendivity testing include applying a flexible sheet over a test article to form a sealed space between the flexible sheet and a surface region of the test article. Methods further include filling the sealed space with an indicator gas mixture, applying an energy discharge to the test article, and determining whether the indicator gas mixture in the sealed space reacted in response to the energy discharge. The indicator gas mixture may be flammable and may be formed while filling the sealed space. Incendivity test systems include the test article, the flexible sheet sealed to the test article to form the sealed space, a gas control module configured to fill, flush, purge, and/or sample gas in the sealed space, and an energy source configured to apply the energy discharge to the test article.

26 Claims, 3 Drawing Sheets

(56) References Cited

OTHER PUBLICATIONS

Section 7.7 of Aircraft Lightning Test Methods, SAE International, ARP5416A, pp. 99-105, undated.
Shepard et al., "*Spark Ignition Energy Measurements in Jet A*," Explosion Dynamics Laboratory Report FM97-9, Graduate Aeronautical Laboratories, California Institute of Technology, May 3, 1999, revised Jan. 24, 2000.
Jaeger et al., "*Prevent Explosions of Combustible Dusts*," Chemical Engineering Progress, Jun. 1999.
Crouch, "*Aircraft Fuel System Lightning Protection Design and Qualification Test Procedures Development*," Technical Report, DOT/FAA/CT-94/74, Sep. 1994.
Bundy et al., "*Full-Scale Flammability Measures for Electronic Equipment*," National Institute of Standards and Technology Technical Note 1461, Aug. 2004.
Williamson et al., "*Ignition Sources in Room Fire Tests and Some Implications for Flame Spread Evaluation*," Fire Safety Science, Proceedings of the Third International Symposium, pp. 657-666, undated.

\* cited by examiner

MOBILE EXPLOSION LAB SYSTEMS AND METHODS FOR INCENDIVITY TESTING

FIELD

The present disclosure relates to systems and methods for mobile explosion lab systems and methods for incendivity testing.

BACKGROUND

In many situations, apparatuses must operate in potentially hazardous conditions, such as where a fuel mixture may be ignited by uncontrolled operating or environmental conditions. For example, vehicles, including aerospace vehicles, typically operate with a fuel that must be maintained in a safe condition during storage and use. The ignition hazard should be minimized even when the vehicle is subject to uncontrolled events such as an accident, electrical malfunction, a lightning strike, or static electrical discharge. Other applications requiring ignition hazard consideration include fuel transport, fuel storage, mining operations, chemical processing, metal fabrication, power plant construction and operation, and operations which involve combustible particulate such as sawdust, metal, flour, and grain.

Design of apparatuses exposed to ignition hazards typically involves reducing the likelihood of ignition, containing the ignition hazard, and/or withstanding the ignition hazard. Test systems may facilitate or verify the design of a component by simulating or applying ignition hazard precursors such as heating, a simulated lightning strike, or other electromagnetic effects (e.g., arcing, electrostatic discharge, and/or hot particle ejection).

In the aerospace industry, the Federal Aviation Administration (FAA) requires ignition source tests for components potentially exposed to fuel-vapor environments (specified in SAE ARP 5416A (SAE Aerospace)). One test method is the ignitable mixture (flammable gas) test method. In the ignitable mixture (flammable gas) test method, a test article that represents the component is subjected to an ignition hazard precursor (e.g., simulated lightning strike) in a flammable atmosphere within a test chamber. If the test article produces an ignition hazard (electrical arc) above a predefined energy limit of 0.2 mJ (millijoules), the flammable atmosphere explosively ignites in the test chamber. The test chamber is designed to enclose the test article such that the flammable atmosphere does not leak and become a hazard, and such that the explosive ignition is contained and rendered non-hazardous.

The drawbacks to this approach include expensive test chambers, limited test article and test chamber sizes (due to both safety and cost), long test setup times (due to filling large volumes with flammable gases), and long preparation times (due to test chamber fabrication).

Further, design of large and complex apparatuses would be facilitated by testing larger and/or more representative test articles (e.g., components or the entirety of a wing fuel tank of an aircraft). However, testing larger articles with conventional techniques involves consequently larger test chambers and/or larger amounts of combustible material (such as fuel in the test article and/or flammable gases to detect ignition sources).

SUMMARY

Methods of incendivity testing according to the present disclosure include applying a flexible sheet over at least a portion of a test article to seal a surface region of the test article from an ambient atmosphere and to form a sealed space between the flexible sheet and the surface region of the test article. Methods further include filling the sealed space with an indicator gas mixture, applying an energy discharge to the test article while the sealed space includes the indicator gas mixture, and determining whether the indicator gas mixture in the sealed space reacted in response to the energy discharge.

Incendivity test systems according to the present disclosure include a test article, a flexible enclosure, an indicator gas mixture, and an energy source. The flexible enclosure includes a flexible sheet sealed over at least a portion of the test article to seal a surface region of the test article from an ambient atmosphere and to form a sealed space between the flexible sheet and the surface region of the test article. The flexible enclosure further includes a gas control module that is configured to fill, flush, purge, and/or sample gas in the sealed space of the flexible enclosure. The energy source is configured to apply an energy discharge to the test article.

The indicator gas mixture may be flammable or non-flammable, and the reaction of the indicator gas mixture due to the energy discharge may be combustion, explosive combustion, and/or thermal decomposition. The indicator gas mixture may be formed while filling the sealed space, e.g., by mixing gas components as the gas components flow into the sealed space. The indicator gas mixture may be formulated to react to an ignition source generated at the surface region of the test article, provided that the ignition source has an energy of greater than or equal to a threshold energy such as 0.2 mJ (as specified in FAA regulations).

DESCRIPTION

Figure 1:
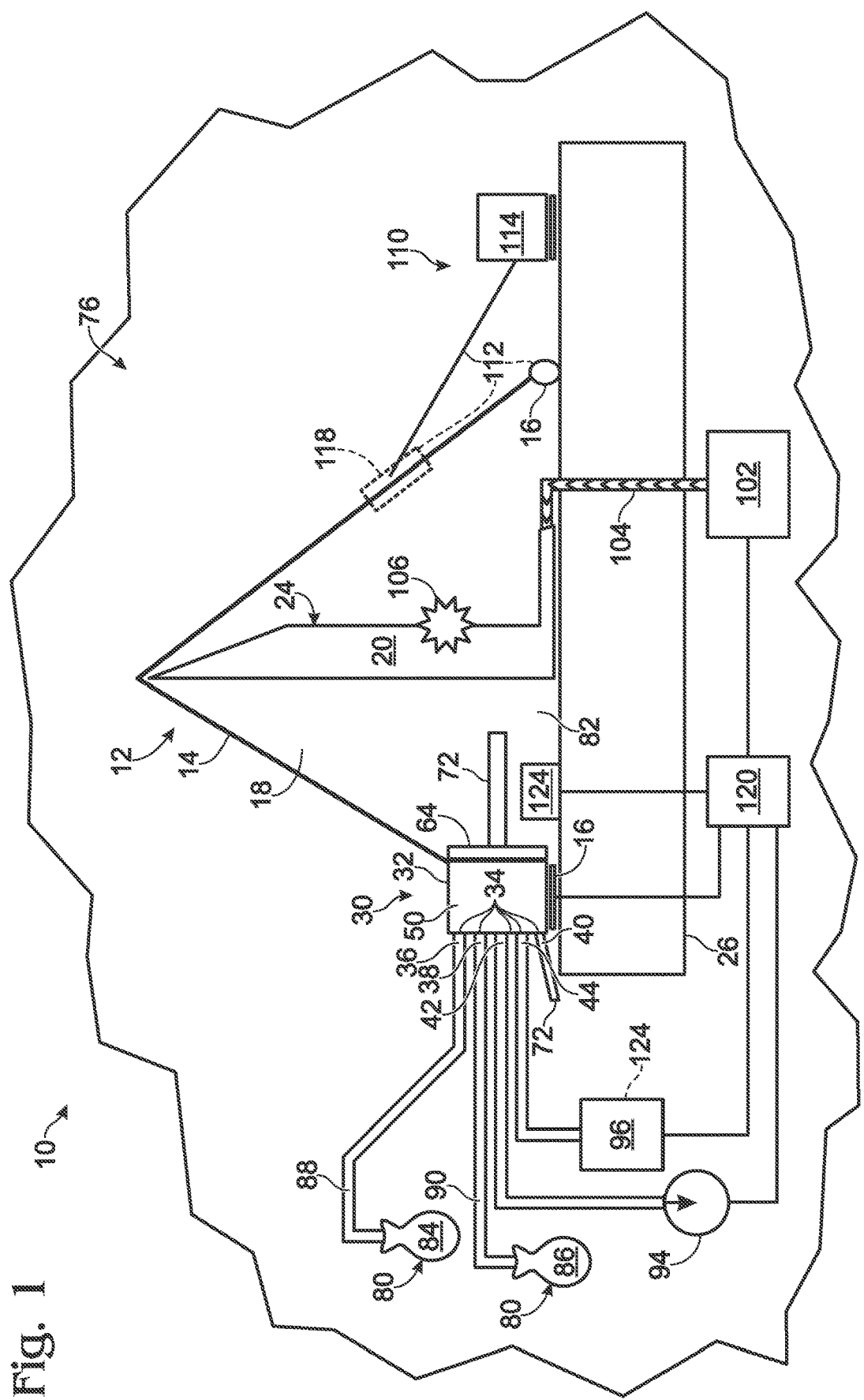
FIG. 1 is a schematic representation of an incendivity test system according to the present disclosure.

The mobile explosion lab systems and methods described herein can be used to test for ignition hazards without the limitations of the traditional ignition hazard testing techniques. In particular, the herein-described systems and methods may be sensitive to various types of ignition hazards on large structures without requiring a test chamber that is similarly large enough to contain the structure. Generally, systems and methods of the present disclosure are designed for versatile test setup and designed to facilitate testing of large test articles (e.g., full scale components and components with multiple, spaced-apart potential ignition hazard sites). For example, test articles may be sealed with a flexible enclosure that is configured for the ignitable mixture (flammable gas) test method. With the flexible enclosure, one need not build or procure a full sized test chamber large enough to enclose the structure and capable of withstanding an explosion of a flammable gas atmosphere. As another example, large structures may have one or more flexible enclosures sealed on or around the structure at a site or sites to be tested. The whole structure does not need to be enclosed in a test chamber capable of withstanding an explosion of a flammable gas atmosphere.

FIGS. 1-4 illustrate incendivity test systems and methods (also referred to as mobile explosion lab systems and methods). In general, in the drawings, elements that are likely to be included in a given embodiment are illustrated in solid lines, while elements that are optional or alternatives are illustrated in dashed lines. However, elements that are illustrated in solid lines are not essential to all embodiments of the present disclosure, and an element shown in solid lines may be omitted from a particular embodiment without departing from the scope of the present disclosure. Elements that serve a similar, or at least substantially similar, purpose are labelled with numbers consistent among the figures. Like numbers in each of the figures, and the corresponding elements, may not be discussed in detail herein with reference to each of the figures. Similarly, all elements may not be labelled or shown in each of the figures, but reference numerals associated therewith may be used for consistency. Elements, components, and/or features that are discussed with reference to one or more of the figures may be included in and/or used with any of the figures without departing from the scope of the present disclosure.

FIG. 1 illustrates a test system 10 that may be utilized to test the incendivity of a test article 20 that is subject to an ignition risk event (an energy discharge). Incendivity is the ability to cause ignition of a flammable substance such as a flammable environment. Hence, the test system 10 may be referred to as an incendivity test system, a flammability test system, an ignition risk test system, and/or an ignition hazard test system. The test system 10 includes the test article 20 and a flexible enclosure 12 formed at least in part by a flexible sheet 14 sealed over at least a portion of the test article 20. The test system 10 generally includes an indicator gas mixture 82 in a sealed space 18 of the flexible enclosure 12 and includes an energy source 102 to apply the energy discharge to the test article 20 and potentially produce an ignition source 106 within the sealed space 18 containing the indicator gas mixture 82. The indicator gas mixture 82 may be a flammable or non-flammable gas mixture formulated to sense the ignition source 106 if it is produced by the energy discharge.

Generally, the test system 10 is configured to identify the presence of, and/or verify the absence of, ignition sources 106 associated with equipment, devices, and/or apparatuses operated in a combustible environment and/or near combustible materials. More specifically, the test system 10 may be configured to detect ignition sources 106 generated on the test article 20 by an ignition risk event (the energy discharge generated by the energy source 102) that simulates actual and/or potential operating conditions and/or uncontrolled events. For example, the energy discharge may be a simulated lightning strike, heat, an electrical discharge, an electrical voltage, an electrical current, an electrical arc, and/or a combustion event (e.g., flame, fire). Examples of ignition sources 106 that may be generated include an electrical arc, a spark, a hot surface, a hot particle ejection, an electrostatic discharge, and a flame.

The test article 20 may be equipment, a device, and/or an apparatus that may operate near combustible materials and/or in combustible environments where uncontrolled ignition sources could be hazardous. The test article 20 also may be a portion, a component, and/or a model of such equipment, device, and/or apparatus. The equipment, device, and/or apparatus may be associated with one or more industries such as transportation, aerospace, chemical processing, petroleum production, mining, power production, forestry, and/or agriculture. For example, the test article 20 may be a transport vehicle (e.g., a truck, an aircraft, a rocket), an aerospace component, a wing, a fuselage, an empennage, an aircraft skin, an aircraft frame, a fuel system, a fuel tank, a fuel pump, a ventilator component, a ventilation system, mining equipment, dust handling equipment, and/or an electrical enclosure. In some instances, the test article 20 may represent and/or may be a component of the above examples.

Generally, the test article 20 has a solid form, though the test article 20 may include liquid and/or gaseous elements. The test article 20 may include one or more of metal, aluminum, plastic, and fiber-reinforced composite material (e.g., carbon fiber reinforced composite material). In particular, the test article 20 may be formed of the materials used for the corresponding equipment, device, and/or apparatus. Materials, equipment, devices, and/or apparatuses that include substantial amounts of non-conductive (or less than the high conductivity of electrically-conductive metals) components may be more prone to electrical related ignition hazards than corresponding materials, equipment, devices, and/or apparatuses that include less of such components. The test article 20 may have a fluidically isolated interior (e.g., the test article 20 includes a tank, a chamber, a canister, a vessel) and the flexible enclosure(s) 12 may be applied to regions of one or both of the interior and exterior of the test article 20 to test for ignition sources 106 that may form inside the test article 20 and/or at the exterior surface of the test article 20.

The energy source 102 is configured to discharge energy into, at, and/or to the test article 20 to test whether the discharged energy generates the ignition source 106 at the test article 20. The energy source 102 may be a simulated or actual operating condition such as a lightning strike, an electrical charge simulating static charge build-up, heat simulating environmental conditions (e.g., ambient operating conditions, proximate decomposition and/or combustion, and/or operation of a neighboring engine), and/or electromagnetic radiation simulating an operating environment. The energy source 102 may include, and/or may be, a lightning simulator, a heater, a heat source, a flame, an electrical power source, an electrical voltage source, an electrical current source, and/or an electrical arc generator. In FIG. 1, the discharged energy is indicated by energy transmission 104. Energy transmission 104 may be via a conduit, a cable, and/or a conductor, and may span a gap between the energy source 102 and the test article 20. The energy source 102 may be separated and/or external from the test article 20 (as illustrated in the example of FIG. 1). In some embodiments, the test article 20 may include the energy source 102 and/or the test article 20 may be the energy source 102 (for example, a test article 20 may include a battery and the test system 10 may be configured to test the battery under normal operating conditions).

The test system 10 and/or the energy source 102 are configured to avoid directly reacting the indicator gas mixture 82 with the energy discharge. In one arrangement, the test system 10 and/or the energy source 102 may be configured to apply the energy discharge to the test article 20 at an application site isolated from the flexible enclosure 12 and/or the indicator gas mixture 82. For example, the energy transmission 104 may include electrical cables which convey a voltage and/or carry a current, and that are electrically isolated from the flexible enclosure 12. As another example, the energy source 102 may be configured to apply the energy discharge to the test article 20 at a site distant from the flexible enclosure(s) 12. The energy from the energy source 102 may traverse and/or may distribute through the test article 20 to the surface region(s) 24. As yet another example, the energy transmission 104 may pass into the flexible enclosure 12 to the test article 20 via electrical cable or other conduit that is electrically isolated from the indicator gas mixture 82.

The test system 10 includes one or more flexible enclosures 12 that each enclose a sealed space 18 that includes a surface region 24 of the test article 20. Flexible enclosures 12 may be referred to as flexible test chambers and/or test cells. The surface region 24 may include a structure, a component, or other potential ignition source generator at, or associated with, the surface of the test article 20. For example, the surface region 24 may include a fastener, a connector, a seam and/or a joint between skin panels, a protrusion, a conduit, a conduit coupler, a corner, an edge, an electronic component (e.g., an electronics module, a controller, or a sensor), and/or a mechanical component (e.g., a vent, a fan, a sensor, a cover, or a panel).

Each flexible enclosure 12 is configured to hold the indicator gas mixture 82 in the sealed space 18 and/or to fluidically isolate the surface region 24 of the test article 20 from an ambient atmosphere 76. The ambient atmosphere 76 may be inert, flammable, or reactive. Examples of constituents or the entirety of the ambient atmosphere 76 include air, molecular oxygen, flammable gas, an inert gas, nitrogen, and/or argon. The ambient atmosphere 76 may be environmental air (uncontained). Additionally or alternatively, all or a portion of the ambient atmosphere 76 may be within a chamber that surrounds and/or incorporates the flexible enclosure 12.

Figure 2:
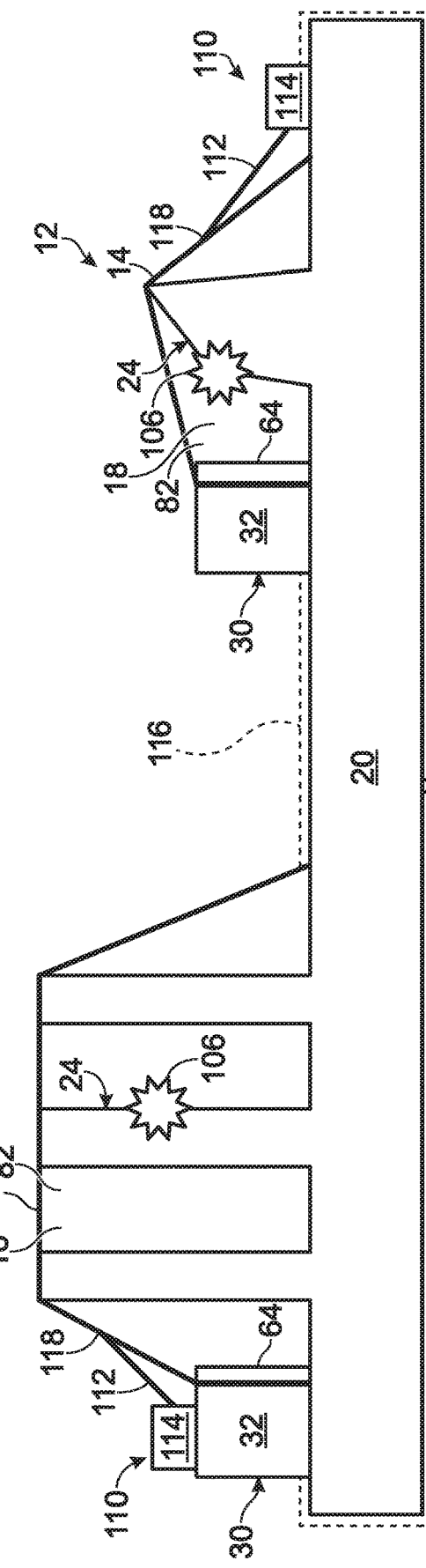
FIG. 2 is a schematic representation of an example of an incendivity test system with two flexible enclosures installed on one test article.

For test systems 10 that include more than one flexible enclosure 12 (as shown in the example of FIG. 2), each flexible enclosure 12 encloses a different portion of the test article 20 (e.g., different surface regions 24). The sealed spaces 18 of the flexible enclosures 12 are fluidically isolated from the ambient atmosphere 76 and each other. Portions of the test article 20 not part of the surface region(s) 24 and/or outside of the flexible enclosure(s) 12 (if any portion of the test article 20 is not enclosed) may be masked, covered, or otherwise isolated from the ambient atmosphere 76. In particular, known ignition sources or sites of likely ignition source formation on the test article 20 may be masked, covered, and/or isolated to suppress ignition source formation outside of the surface region(s) 24 of the test article 20. Hence, the masked, covered, and/or isolated regions would not interfere with the testing of the surface region(s) 24 in the flexible enclosure(s) 12. In FIG. 2, an optional mask 116 is schematically represented as applied to the portions of the test article 20 that are outside of the flexible enclosures 12.

The flexible enclosure 12 is formed by applying a flexible sheet 14 over at least a portion of the test article 20 that includes the surface region 24. The flexible sheet 14 is a flexible material that is in a sheet, membrane, film, layer, or similar form. The flexible sheet 14 generally is thin, for example having a thickness of less than 1 mm, less than 0.5 mm, less than 0.2 mm, less than 0.02 mm, greater than 0.001 mm, and/or greater than 0.01 mm.

The flexible sheet 14 may be elastic or inelastic. An elastic flexible sheet 14 may substantially maintain pressure within the flexible enclosure 12 (e.g., maintaining the pressure within the flexible enclosure 12 at about the pressure of the ambient atmosphere 76). An inelastic flexible sheet 14 may substantially maintain volume within the flexible enclosure 12. The flexible sheet 14 may include one or more layers that each independently include (and any of the layers may be composed of) plastic, metalized plastic film, polyester, polyethylene, polypropylene, polyethylene terephthalate (PET), biaxially-oriented polyethylene terephthalate, polyamide, polyimide, rubber, synthetic rubber, polyurethane, polymers of isoprene, polymers of butadiene, and polymers of styrene. Examples of flexible sheet 14 materials include MYLAR brand film, NYLON brand film, rubber sheet, and vacuum bagging materials as used for production of composite materials.

The flexible sheet 14 is at least substantially impermeant to gas. Generally, the gas permeability of the flexible sheet 14 is low enough to maintain the pressure and composition of the indicator gas mixture 82 for the duration of the testing. The gas permeability may be very low. For example, the oxygen transmission rate through the flexible sheet 14 may be less than 10 mL/m$^2$/day (milliliters per meter squared per day), less than 1 mL/m$^2$/day, or less than 0.1 mL/m$^2$/day (as measured at standard pressure and temperature).

To form the flexible enclosure 12, the flexible sheet 14 is sealed to itself and/or other components, e.g., the test article 20, a base 26 that supports the test article 20 (also called a substructure; shown schematically in FIG. 1), or another flexible sheet 14. In some embodiments, the flexible sheet 14 may form a sealed bag around the test article 20. The flexible sheet 14 and/or the flexible enclosure 12 may at least partially enclose one or more other components of the test system 10. For example, the energy source 102 may be within the flexible enclosure 12. The flexible sheet 14 may be formed of one or more panels of flexible, sheet-like materials. The panels may be bonded, fused, fastened, or otherwise secured together to form the flexible sheet 14.

The flexible sheet 14 may be sealed to itself or other components with one or more seals 16. Where flexible sheets 14 include one or more panels or layers, the panels or layers may be secured together with one or more seals 16. Seals 16 may include, and/or may be, an adhesive, a mastic, a bond, a weld, and/or a clamp. The seal 16 may be essentially permanent or temporary, and may be removable and/or breakable. Different portions of flexible sheet 14 may be sealed with different types of seals 16. The seals 16 are sufficiently gas tight and vacuum tight to permit the flexible enclosure to be filled with a gas (e.g., the indicator gas mixture 82) and to be evacuated of the gas. The seals 16 are sufficiently gas tight to maintain a gas pressure of about 100 kPa (kilopascals) and sufficiently vacuum tight to maintain a gas pressure of about 1 kPa.

The indicator gas mixture 82 is configured, selected, and/or formulated to react in response to the ignition source 106 at the surface region 24 of the test article 20, if any ignition source 106 is produced by the energy discharge by the energy source 102. The indicator gas mixture 82 may be configured, selected, and/or formulated to react in response to ignition sources 106 of particular types (e.g., electrical arc, hot particle emission, hot surface) and/or at or above a threshold energy level or temperature at suitable environmental conditions. Examples of a threshold energy level include the equivalent energy specified in the FAA regulations (i.e., 0.2 mJ for an electrical arc) or other standardized tests, e.g., an energy equivalent to an electrical arc with an energy of less than 1 mJ, less than 0.5 mJ, greater than 0.01 mJ, greater than 0.1 mJ, and/or about 0.2 mJ. Examples of a threshold temperature include the temperature of known ignition hazards, e.g., greater than 200° C., greater than 300° C., or greater than 500° C. Suitable environmental conditions are as described further herein with respect to testing. The selection, formulation, and/or composition of the indicator gas mixture 82 and its components may affect the threshold energy level and/or threshold temperature. The minimum threshold energy level and/or temperature of the indicator gas mixture 82 may be calibrated and/or verified by subjecting the indicator gas mixture 82 to a controlled-energy ignition source such as a controlled electrical arc of known stored energy and/or known discharge energy.

The indicator gas mixture 82 may be flammable. In which case, the indicator gas mixture 82 may combust or explosively combust in response to the ignition source 106. The indicator gas mixture 82 may be non-flammable and include a thermally reactive reagent that is configured, selected, and/or formulated to react (e.g., combust and/or thermally decompose) in response to the ignition source 106. The combustion or other reaction of the indicator gas mixture 82 may be monitored and/or the resulting gas may be analyzed to verify the presence of an ignition source 106. For flammable gas mixtures, the combustion reaction of the indicator gas mixture 82 may be substantially complete (e.g., all or most of the reactants are reacted). For non-flammable gas mixtures, the extent of reaction of the thermally reactive reagent may be related (e.g., proportional) to the energy and/or character of the ignition source 106.

The indicator gas mixture 82 may include a fuel and/or an oxidant (also called an oxidizer). The fuel is a combustion fuel, i.e., a reagent that combusts in the presence of the oxidant. Examples of the fuel include a hydrocarbon fuel, a flammable gas, molecular hydrogen, methane, propane, gasoline, kerosene, and ethylene. Examples of the oxidant include molecular oxygen, nitrous oxide, and hydrogen peroxide.

The thermally reactive reagent may be the fuel, the oxidant, or another chemical species that undergoes thermal decomposition or other reaction. Other examples of the thermally reactive reagent include a halocarbon (a compound with a halogen-carbon bond) such as an alkyl halide, a chlorocarbon, a fluorocarbon, a bromocarbon, a chlorofluorocarbon, chloroethane, and methyl bromide. Halocarbons combust and/or thermally decompose to produce relatively uncommon reaction products that may be detected by gas analysis.

The indicator gas mixture 82 is generally gaseous and may include gas and/or an aerosol of liquids and/or solids (e.g., the indicator gas mixture 82 may include an aerosol of the fuel, the oxidant, and/or the thermally reactive reagent). The fuel, the oxidant, and/or the thermally reactive reagent may be in the form of a gas, a vapor, and/or an aerosol.

The indicator gas mixture 82 may include a diluent. The diluent is generally a gas and does not significantly participate in the reaction of the indicator gas mixture 82 in response to the ignition source 106. Generally, the diluent is inert and/or non-reactive. The diluent may be selected, configured, and/or formulated for lack of reactivity with other components of the indicator gas mixture 82. The diluent may be selected, configured, and/or formulated to quench (or enhance) combustion and/or a flame front in the indicator gas mixture 82. For example, the diluent may have a high heat capacity and/or a low thermal conductivity which may limit the flammability of the indicator gas mixture 82. As another example, the diluent may have a low heat capacity and/or a high thermal conductivity which may enhance the flammability of the indicator gas mixture 82. The diluent may be a gas including one or more of an inert gas, nitrogen, argon, and/or helium.

Mixtures of fuels and oxidants have a flammability range in which the mixture may be ignited (at a given pressure and temperature). Outside of the flammability range, the mixture cannot be ignited, without changing the conditions such as increasing the temperature and/or the pressure. The flammability range may be expressed as a ratio of the fuel to oxidant concentrations, and/or a concentration range of the fuel in an oxidant-fuel mixture. An oxidant-fuel mixture has a stoichiometric ratio for complete burning of the oxidant and the fuel. If the amount of fuel is below the stoichiometric amount, the mixture is called lean. If the amount of fuel is above the stoichiometric amount, the mixture is called rich. Unless otherwise stated, the flammability range as used herein is expressed as a mass concentration ratio of fuel to oxidant.

The flammability range is delineated by a lower flammability limit (also called a lean ignition limit) and an upper flammability limit (also called a rich ignition limit). Below the lower flammability limit, the oxidant-fuel mixture does not contain enough fuel to support a self-propagating combustion wave. Above the upper flammability limit, the oxidant-fuel mixture does not contain enough oxidant to support a self-propagating combustion wave.

Flammable or non-flammable indicator gas mixtures 82 may be configured, selected, and/or formulated to be near or below the lower flammability limit to reduce the possibility of uncontained combustion and/or explosion. If a mixture escapes the test system 10 and/or the flexible enclosure 12, the mixture may be diluted by external gas (such as air). If the indicator gas mixture 82 is near or below the lower flammability limit and is significantly diluted, the indicator gas mixture 82 would become or remain below the lower flammability limit and would become or remain non-flammable.

As shown schematically in FIG. 1, the flexible enclosure 12 includes a gas control module 30 for the introduction and/or removal of gas to and/or from the sealed space 18. For example, the gas control module 30 is configured to fill, flush, purge, and/or sample gas in the sealed space 18. The gas control module 30 includes one or more gas ports 34 that provide fluidic access to the sealed space 18. Each of the gas ports 34 independently may be configured to introduce gas into the sealed space 18, remove gas from the sealed space 18, or both introduce gas to and remove gas from the sealed space 18.

Figure 3:
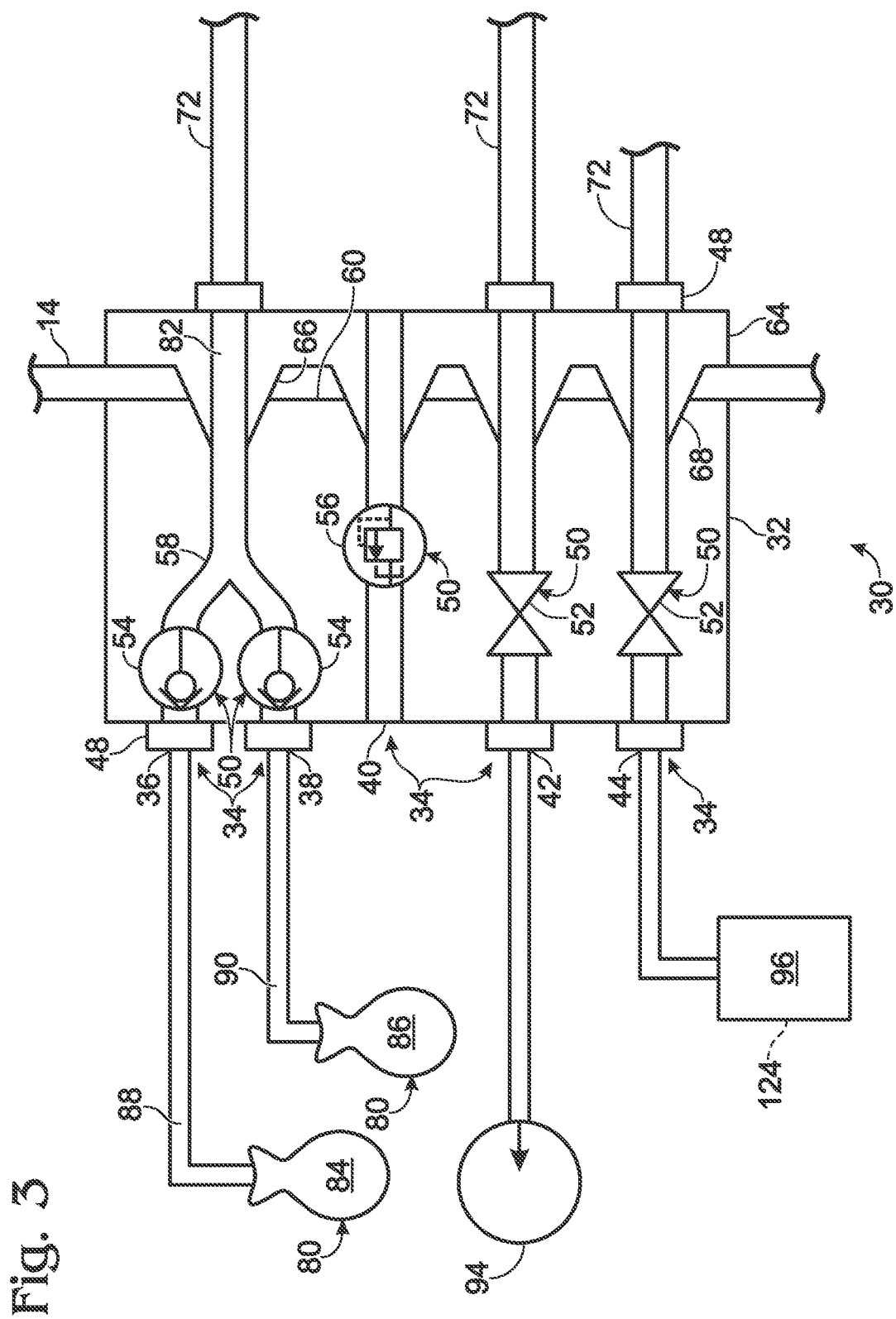
FIG. 3 is a schematic diagram of a gas control module as may be utilized in an incendivity test system according to the present disclosure.

As also shown in FIG. 3, each of the gas ports 34 may be connected to a gas source 80 or other device to introduce and/or remove gas from the sealed space 18. The gas ports 34 may include connectors 48 (FIG. 3) to facilitate connection of tubing to the gas source 80 or other device. The optional connectors 48 may include check valves to seal the associated gas port 34 when not in use. Additionally or alternatively, the gas control module 30 may include one or more valves 50 to control the gas flow through at least one of the gas ports 34. Generally, each of the gas ports 34 is associated with at least one of the valves 50 such that each of the gas ports 34 has at least one valve 50 configured to control the gas flow of that gas port 34. Valves 50, each independently, may include (and/or may be) a stop valve 52, a check valve 54, and/or a pressure relief valve 56. Stop valves 52 are configured to restrict or permit gas flow through the stop valve 52 and generally are configured to adjust the flow through stop valve 52. For example, a stop valve 52 may be arranged to selectively isolate the sealed space 18 of the flexible enclosure 12. Check valves 54 are configured to permit gas flow in one direction through the check valve 54 (i.e., configured to permit flow while a pressure differential across the check valve 54 is maintained). For example, a check valve 54 may be arranged to prevent leakage from the sealed space 18 when no gas is flowing into the sealed space 18 through the check valve 54 from outside of the sealed space 18. Pressure relief valves 56 are configured to permit gas flow through the pressure relief valve 56 if the pressure at an input to the pressure relief valve 56 is greater than a predetermined threshold. For example, a pressure relief valve 56 may be arranged to seal the sealed space 18 unless and/or until the gas pressure in the sealed space 18 exceeds a predetermined threshold. Thus, pressure relief valves 56 may protect from over-pressurization of the flexible enclosure 12.

Each gas source 80 may include a pressure vessel and/or a gas generation apparatus. The gas supplied may be the indicator gas mixture 82 and/or constituents of the indicator gas mixture 82 such as oxidant, fuel, thermally reactive reagent, and diluent. For example, gas with oxidant 88 (i.e., a gas that includes oxidant as a gas and/or an aerosol, and which may be a pure gas of oxidant or a mixture of gases and/or aerosol components that include oxidant) may be supplied to an oxidant port 36 (one of the gas ports 34) from an oxidant source 84 (one of the gas sources 80). As another example, gas with fuel 90 (i.e., a gas that includes fuel as a gas and/or an aerosol, and which may be a pure gas of fuel or a mixture of gases and/or aerosol components that include fuel) may be supplied to a fuel port 38 (one of the gas ports 34) from a fuel source 86 (one of the gas sources 80). Gas ports 34 configured to introduce gas into the sealed space 18 from a gas source 80 may include and/or may be associated with a check valve 54 arranged to permit flow into the sealed space 18 and to restrict flow out of the sealed space 18.

Other types of gas ports 34 include a relief port 40 (also called a pressure relief port), a vacuum port 42 (also called a vent port), and a sample port 44. The relief port 40 is configured to release gas from the sealed space 18 when the pressure in the sealed space 18 is above a predetermined threshold. The relief port 40 may include and/or may be associated with a pressure relief valve 56. Additionally or alternatively, the relief port 40 may include and/or may be associated with a stop valve 52 that is controllable (manually and/or automatically) such that pressure in the sealed space 18 above the predefined threshold may be released. The vacuum port 42 is configured to vent and/or to evacuate the sealed space 18, for example by being connected to unpressurized space (e.g., ambient air) or by being connected to a vacuum source 94. The vacuum source 94 may be a vacuum pump, an evacuated vessel, or other source/repository of low pressure. The vacuum source 94 may have and/or may be configured to produce an absolute pressure of less than 20 kPa, less than 10 kPa, or less than 1 kPa. The vacuum port 42 may include and/or may be associated with a stop valve 52 arranged to selectively isolate the sealed space 18 from the vacuum source 94. The sample port 44 is configured to extract a sample of gas from the sealed space 18. The sample port 44 may include and/or may be associated with a stop valve 52 arranged to selectively isolate the sealed space 18 from the output of the sample port 44 (e.g., a gas sampling system 96 as discussed further herein).

The gas control module 30 may include a gas port 34 that is configured to serve as one or more of the oxidant port 36, the fuel port 38, the relief port 40, the vacuum port 42, and/or the sample port 44. For example, the indicator gas mixture 82 may be introduced into the sealed space 18 through a combined oxidant and fuel port (also called an indicator gas mixture port). Gas flow into or out of the sealed space 18, whether through dedicated gas ports 34 or combined gas ports 34, may be controlled with mass flow controllers and/or external valving and equipment.

In embodiments where the indicator gas mixture 82 is composed of two or more constituents (e.g., a fuel and an oxidant, and optional other components), the constituents may be mixed before introduction into the flexible enclosure 12 and/or two or more of the constituents may be supplied separately to the flexible enclosure 12 (e.g., through the oxidant port 36 for the oxidant and through the fuel port 38 for the fuel). Separately supplied constituents may be mixed as the gases are introduced into the flexible enclosure 12 (e.g., via a gas mixer 58) and/or while the gases are within the sealed space 18 of the flexible enclosure 12. For example, fuel and oxidant may be mixed to form the indicator gas mixture 82 prior to introduction into the flexible enclosure 12 or may be supplied separately to the flexible enclosure 12. The optional gas mixer 58 may include, and/or may be, a mixing manifold with separate inlets for the input gases and a mixed gas outlet for the output gas. The optional gas mixer 58 may include proportional valves and/or mass flow controllers. Mixing of gases within the sealed space 18 may be accomplished with a fan or stirrer within the sealed space 18.

The gas control module 30 may include a body 32 which incorporates one or more of the gas ports 34 and/or one or more of the valves 50 (e.g., all of the gas ports 34 and the valves 50 are in a single body 32). To form the flexible enclosure 12, the body 32 is sealed to the flexible sheet 14 and may be sealed to the test article 20 and/or the base 26. The body 32 may be sealed by a seal 16 as discussed herein.

A portion of the flexible sheet 14 may be sealed to the body 32 with a backing plate 64 configured to clamp the flexible sheet 14 between the body 32 and the backing plate 64. The body 32 and the backing plate 64 each include corresponding seal surfaces, indicated as the body seal surface 60 of the body 32 and the backing plate seal surface 66 of the backing plate 64 in FIG. 3. The body 32 and/or the backing plate 64 (and/or the corresponding body seal surface 60 and/or backing plate seal surface 66) may include one or more engagement elements 68 that are configured to mate with the opposite component and/or seal surface. Engagement elements 68 may be mating elements such as pins, holes, sockets, shoulders, edges, grooves, and/or protrusions. Engagement elements 68 may be configured to align and/or securely mate the body 32 and the backing plate 64.

The backing plate 64 may have through-passages that correspond to the gas ports 34. When the flexible sheet 14 is clamped between the body 32 and the backing plate 64, the flexible sheet 14 has through-passages that correspond to the gas ports 34. Thus, the gas ports 34 extend through the body 32, the flexible sheet 14, and the backing plate 64. The engagement elements 68 of the body 32 and/or of the backing plate 64 (and/or the body seal surface 60 and/or the backing plate seal surface 66 near the gas ports 34) may be configured to puncture and/or pierce the flexible sheet 14 between the body 32 and the backing plate 64. Hence, the body 32 and/or the backing plate 64 may be configured to form the through-passages in the flexible sheet 14 that correspond to the gas ports 34.

Mixing, flushing, filling, and/or purging of the sealed space 18 may be facilitated by extension tubes 72 connected to one or more of the gas ports 34. In particular for gas ports 34 that have opposite potential gas flows (e.g., one gas port 34 introduces gas into the sealed space 18 while another gas port 34 extracts gas from the sealed space 18), the points at which gas enters and exits the sealed space 18 may be separated to avoid significant short circuiting of gas flow from the inlet gas port 34 to the outlet gas port 34. For example, the gas port(s) 34 configured to introduce the indicator gas mixture 82 and/or components of the indicator gas mixture 82 may be connected to an extension tube 72 in the sealed space 18 to arrange the gas outlet of the gas port(s) 34 away from other gas ports 34, e.g., the vacuum port 42. As another example, the vacuum port 42 may be connected to an extension tube 72 to place the inlet to the vacuum port 42 in a location to efficiently evacuate the sealed space 18 near the test article 20. Extension tubes 72 may be used on the external side of the gas ports 34. For example, the relief port 40 may be connected to an extension tube 72 to release gas from the sealed space into a vent or other space located away from the test article 20.

The test system 10 may include a gas sampling system 96 configured to extract a sample of gas from the flexible enclosure and to analyze the sampled gas. The gas sampling system 96 may be configured to sample gas before and/or after application of the energy discharge by the energy source 102. The gas sampling system 96 may be fluidically connected to the sample port 44.

The gas sampling system 96 generally is configured to determine the flammability and/or the chemical composition of the sampled gas. For example, the gas sampling system 96 may be configured to extract a sample of the indicator gas mixture 82 as present in the sealed space 18 before and/or after the energy discharge. The sample of indicator gas mixture 82 may be subjected to a controlled ignition source 124 (an energy source configured to reliably discharge energy into a gas) to verify that the indicator gas mixture 82 is flammable. The controlled ignition source 124 may be configured to produce an electrical arc, a spark, a hot surface, a hot particle ejection, an electrostatic discharge, and/or a flame. The controlled ignition source 124 may include, and/or may be, a heater, a heat source, a flame, an electrical current source, and/or an electrical arc generator. The controlled ignition source 124 may be configured to discharge a controlled-energy discharge (having a known and/or repeatable amount of energy) into the sample gas. The controlled ignition source 124 may be configured to discharge an electrical arc having the energy specified in the FAA regulations (i.e., 0.2 mJ) or other standardized tests, e.g., less than 1 mJ, less than 0.5 mJ, greater than 0.01 mJ, greater than 0.1 mJ, and/or about 0.2 mJ. Additionally or alternatively, the test system 10 may include a controlled ignition source 124 within the flexible enclosure 12. After applying the discharge energy to the test article 20, if the indicator gas mixture 82 does not react, the controlled ignition source 124 (in the flexible enclosure 12 or in the gas sampling system 96) may be used to verify that the indicator gas mixture 82 is reactive (e.g., combustible) at the energy of the controlled ignition source 124.

As another example of the gas sampling system 96, in embodiments where the indicator gas mixture 82 is selected, configured, and/or formulated to be non-flammable, the gas sampling system 96 may be configured to extract a sample of the indicator gas mixture 82 before and/or after application of the energy discharge and potential reaction due to the ignition source 106 (if any). The sample of the indicator gas mixture 82 and/or the sample of the potentially reacted indicator gas mixture 82 may be analyzed for one or more gas components with a gas analyzer. The gas analyzer may be used to determine the amount and/or relative amount of one or more components of the gas sample. Examples of gas analyzers include a mass spectrometer, a gas chromatography apparatus, a gas chromatography mass spectrometer, and/or an optical spectrometer. Optical spectrometers may be configured to measure absorbance, transmittance, reflectance, scattering, spectrum, luminescence, fluorescence, and/or phosphorescence. Examples of optical spectrometers include a laser-induced fluorescence (LIF) apparatus, a planar laser-induced fluorescence (PLIF) apparatus, a laser-excited atomic fluorescence (LEAF) apparatus, and a Fourier transform infrared (FTIR) spectrometer.

In some embodiments, the gas sampling system 96 and/or the gas analyzer may be sensitive to small changes in chemical composition of the indicator gas mixture 82. If the indicator gas mixture 82 is non-flammable or the combustion due to the ignition source 106 is otherwise quenched, only a portion of the indicator gas mixture 82 will react in response to the ignition source 106 at the test article 20 in the sealed space 18. The portion is related to the physical size of the ignition source 106, the duration of the ignition source 106, and the energy content of the ignition source 106. In this embodiment, the reactive components in the indicator gas mixture 82 (e.g., the fuel, the oxidant, and/or the thermally reactive reagent) will react in a localized, relatively small volume that is related to the size and energy content of the ignition source 106 and the nature of the reaction (e.g., combustion and/or thermal decomposition) of the indicator gas mixture 82. The reaction volume may be referred to as a reaction kernel and/or a combustion kernel. The reaction volume may be less than 10 mL (milliliter), less than 1 mL, or less than 0.1 mL, and typically is greater than 0.000001 mL (1 nanoliter). The total volume of the indicator gas mixture 82 in contact with the test article 20 in one of the flexible enclosures 12 is related to the size of the corresponding surface region 24 of the test article 20. Some test articles 20 may be very large (e.g., an aircraft wing) and may include correspondingly large structure to be tested within a flexible enclosure 12. Typical volumes of the sealed space 18 of the flexible enclosure 12 (filled with indicator gas mixture 82) include greater than 0.1 L (liter), greater than 1 L, greater than 10 L, and typically less than 1,000 L (1 cubic meter). Thus, the reaction volume of the indicator gas mixture 82 may be less than one thousandth or less than one millionth of the total volume of the indicator gas mixture 82.

Because of the small reaction volume of the indicator gas mixture 82 and because each of the reactive components may be included in the indicator gas mixture 82 at a volume concentration of less than 50% (or less than 10%, or less than 1%), the reactive components and/or reaction products may have a change in concentration, relative to the indicator gas mixture 82 before the energy discharge, that may be in the range of parts per million or parts per billion. Hence, the gas sampling system 96 may be configured to measure concentrations and/or absolute changes in concentrations at the level of parts per million or parts per billion.

As schematically illustrated in FIGS. 1 and 2, test systems 10 may include one or more indicator modules 110. Each flexible enclosure 12 may have one or more associated indicator modules 110. The indicator module 110 is configured to change physical state in response to reaction of the indicator gas mixture 82 in the sealed space 18 due to the energy discharge. Additionally or alternatively, the indicator module 110 may be configured to change the physical state of one or more elements of the flexible enclosure 12 (e.g., rupturing the flexible sheet 14 and/or the seal 16).

The indicator module 110 may be in contact (thermally and/or mechanically) with at least one of the flexible sheet 14 and the indicator gas mixture 82 in the sealed space 18 to sense the reaction of the indicator gas mixture 82 in the sealed space 18. The reaction of the indicator gas mixture 82 in the sealed space 18 may be combustion, explosive combustion, exothermic reaction, endothermic reaction, and/or other reactions with a significant release or absorption of energy as compared with the energy of the ignition source 106. For example, combustion may produce significant heat, light, and pressure within the flexible enclosure 12. The energy of the reaction of the indicator gas mixture 82 may manifest as a displacement, pressurization, heating, and/or cooling of the flexible enclosure 12. For example, a flexible enclosure 12 that includes substantially inelastic elements (e.g., includes flexible sheets 14 that are inelastic) may become pressurized in response to a combustion of the indicator gas mixture 82 in the sealed space 18. As another example, a flexible enclosure 12 that includes an elastic element (e.g., includes a flexible sheet 14 that is elastic) may change volume in response to a combustion of the indicator gas mixture 82 in the sealed space 18.

The physical state change of the indicator module 110 is a mechanical or chemical state change that persists after the test article 20 in contact with the indicator gas mixture 82 has been subject to the energy discharge. Hence, the operator of the test system 10 may have a reliable indicator of reaction of the indicator gas 82 (or lack thereof) that is not subject to significant interference from the energy discharge itself. For example, electronic sensors placed in proximity to the test article and arranged to measure a reaction of the indicator gas mixture 82 in response to the energy discharge from the energy source 102 may be affected by the energy discharge, in particular in embodiments where the energy discharge is or includes a large electrical current, electrical voltage, or electrical impulse. In contrast to electronic sensors, the physical state change records the presence of the event (e.g., explosive combustion) or energy (e.g., heat and/or pressure of an explosive combustion event) necessary to cause the physical state change without interference from the energy discharge itself. Examples of physical state changes include a position, a conformation, a phase of matter, and a chemical composition. Generally, the indicator module 110 is configured to visually indicate the reaction of the indicator gas mixture 82 in the sealed space 18 (e.g., the physical state change is a visibly identifiable change).

The indicator module 110 includes an indicator element 112 and generally a base 114 configured to support and/or contain the indicator element 112. Generally, the indicator element 112 is in contact with the flexible sheet 14 and/or the indicator gas mixture 82. The indicator element 112 is configured to experience the physical state change in response to reaction of the indicator gas mixture 82 in the sealed space 18.

Examples of indicator elements 112 include a frangible element, a deformable element, a displaceable element, a piercing element, and/or a phase-change element. A frangible indicator element 112 is configured to break in response to the reaction of the indicator gas mixture 82 in the sealed space 18. For example, the frangible indicator element 112 may be a thin strap coupled to the flexible sheet 14 and to a fixed object such as the test article 20 or the base 26. Relative displacement between the flexible sheet 14 and the fixed object may cause the strap to break. As another example, the frangible indicator element 112 may be one or more of the seals 16 that seal the flexible sheet 14 to form the flexible enclosure 12. Volume and/or pressure changes within the sealed space 18 may cause the seal 16 to lose integrity and/or the flexible sheet 14 to become loose. As yet another example, the frangible indicator element 112 may be a frangible zone 118 in the flexible sheet 14. The frangible zone 118 may be a thinner section of the flexible sheet 14, a weakened section of the flexible sheet 14, a scored and/or scratched section of the flexible sheet 14, and/or a panel covering a hole in the flexible sheet 14 that is sealed to the flexible sheet 14 by a frangible seal. In some embodiments, the flexible sheet 14 is frangible and hence, the frangible zone 118 may be all or substantially all of the flexible sheet 14. Volume and/or pressure changes within the sealed space 18 may cause the frangible zone 118 to break and thereby cause the flexible enclosure 12 to lose its sealed state.

A deformable indicator element 112 is configured to plastically deform in response to reaction of the indicator gas mixture 82 in the sealed space 18. For example, the deformable indicator element 112 may be a thin wire coupled to the flexible sheet 14 and to a fixed object such as the test article 20 or the base 26. Relative displacement between the flexible sheet 14 and the fixed object may cause the wire to deform (e.g., to bend, uncoil, coil, etc.).

A displaceable indicator element 112 is configured to stably displace in response to reaction of the indicator gas mixture 82 in the sealed space 18. For example, the displaceable indicator element 112 may include a maximum displacement indicator that may undergo unidirectional displacement in response to relative displacement between the flexible sheet 14 and a fixed object. Maximum displacement indicators are typically used on measurement gauges (typically linear or rotary mechanical gauges) to indicate the maximum displacement of a needle or other measurement indicator along the gauge. The maximum displacement indicator may include, and/or may be, one or both of a friction-stiction device (moving in response to the measurement indicator and retaining the last position by friction when not in contact with the measurement indicator) and a ratcheting device (moving in response to the measurement indicator and restricted in reverse movement by a pawl). Ratcheting devices may be rotary (e.g., incorporating a gear and pawl) and/or linear (e.g., incorporating a toothed rack and pawl (like a cable tie)). Additionally or alternatively, the pressure relief valve 56 may be the displaceable indicator element 112. Pressure changes within the sealed space 18 may cause the pressure relief valve 56 to release at least a portion of the indicator gas mixture 82 from the flexible enclosure 12. The pressure relief valve 56 may include a trip indicator that visibly indicates if the pressure relief valve 56 is or was activated to release gas.

A piercing indicator element 112 is configured to rupture the flexible sheet 14 in response to reaction of the indicator gas mixture 82 in the sealed space 18. For example, the piercing indicator element 112 may be a sharp tip which is arranged in close proximity to the flexible sheet 14 (or in contact with the flexible sheet 14). Relative displacement of the flexible sheet 14 towards the sharp tip may cause the sharp tip to pierce and/or rupture the flexible sheet 14 and thereby cause the flexible enclosure 12 to lose its sealed state.

A phase-change indicator element 112 is configured change from a solid to a liquid and/or a gas (or vice versa) in response to reaction of the indicator gas mixture 82 in the sealed space 18. For example, the phase-change indicator element 112 may be a solid material in thermal contact with the indicator gas mixture 82 that is in the sealed space 18. Combustion of the indicator gas mixture 82 may release sufficient heat to melt the solid material and permit the melted solid material to flow into a different position.

The test system 10 may include a controller 120 configured and/or programmed to control the operation of the test system 10 as a whole and/or individual components of the test system 10. The controller 120 may be configured and/or programmed (a) to discharge the energy source 102 to apply the energy discharge to the test article 20, (b) to operate one or more valves 50, (c) to operate the gas source(s) 80, the vacuum source 94, the gas sampling system 96, and/or the controlled ignition source 124, and/or (d) to determine whether a reaction of the indicator gas mixture 82 occurred in response to the energy discharge of the energy source 102. The controller 120 may be configured and/or programmed to perform any of the methods described herein. The controller 120 may include a computer, an embedded controller, a programmable logic device, and/or a field-programmable gate array.

To perform a test with the test system 10, the surface region 24 of the test article 20 is isolated in the flexible enclosure 12, the indicator gas mixture 82 is introduced into the flexible enclosure 12, the test article 20 in contact with the indicator gas mixture 82 is placed in suitable environmental conditions, and the energy discharge is applied with the energy source 102. Suitable environmental conditions include pressure of the indicator gas mixture 82 and temperature of the test system 10. Suitable environmental conditions may include standard pressure and temperature, reduced pressure and/or temperature as compared to standard pressure and temperature, and/or elevated pressure and/or temperature as compared to standard pressure and temperature corresponding to operating and/or storage conditions of the test article 20 (or equipment, devices, and/or apparatuses represented by the test article 20). Suitable environmental conditions may simulate environments such as operating and/or storage conditions on the surface of the Earth (e.g., hot conditions in hot climates, cold conditions in cold climates), in the sky (e.g., cold and low pressure conditions at altitude), and/or below ground (e.g., hot conditions in tunnels). For example, suitable conditions may include a temperature of less than 200° C., less than 150° C., less than 100° C., less than 80° C., less than 50° C., less than 30° C., greater than −40° C., greater than −20° C., greater than 0° C., greater than 10° C., about 0° C., about 20° C., about 25° C., about 40° C., about 70° C., and/or about 100° C. Suitable conditions may include a pressure of the indicator gas mixture 82 of greater than 50 kPa, greater than 70 kPa, greater than 90 kPa, greater than 100 kPa, greater than 110 kPa, less than 200 kPa, less than 150 kPa, less than 120 kPa, less than 100 kPa, about 90 kPa, about 100 kPa, and/or about 110 kPa.

Figure 4:
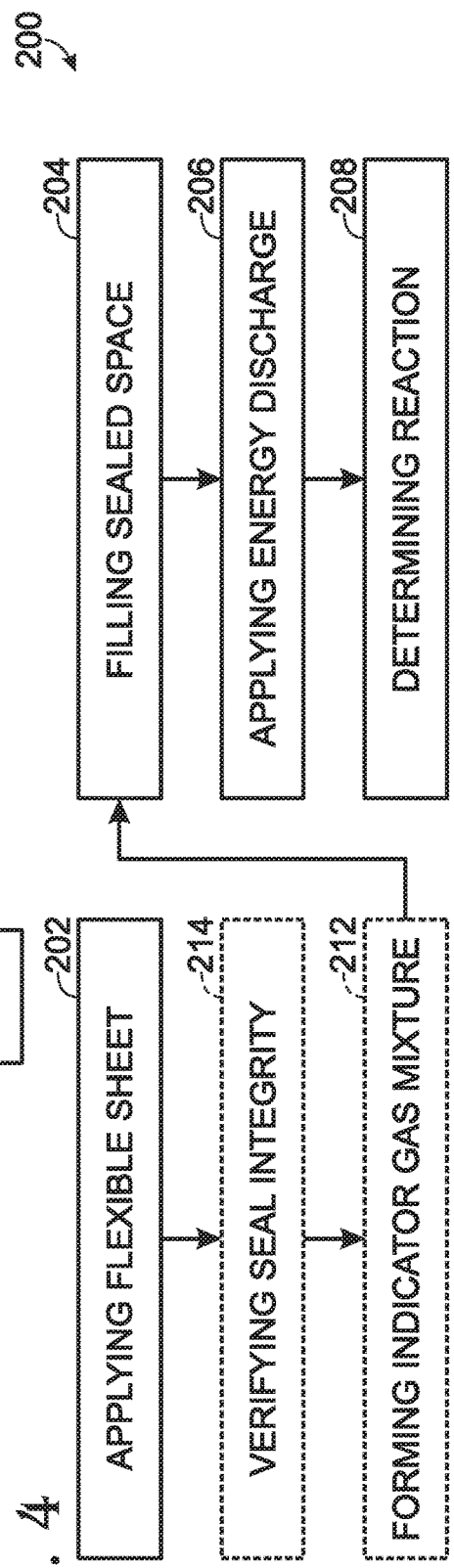
FIG. 4 is a schematic representation of incendivity test methods according to the present disclosure.

FIG. 4 illustrates incendivity test methods 200. Methods 200 may be referred to as flammability test methods, ignition risk test methods, and/or ignition hazard test methods. Methods 200 may be methods of testing test articles for proper operation (e.g., verification of no generated ignition sources), for robustness to operation conditions (e.g., resilience to heat, motion, electrical discharge, etc.), and/or for robustness in failure conditions (e.g., due to accident, proximate fire, lightning strike, etc.). Methods 200 include applying 202 a flexible sheet (such as flexible sheet 14) to form a sealed space (such as sealed space 18) at the surface of a test article (such as test article 20), filling 204 the sealed space with an indicator gas mixture (such as indicator gas mixture 82), applying 206 an energy discharge to the test article, and determining 208 whether the indicator gas mixture in the sealed space reacted in response to the energy discharge.

Applying 202 the flexible sheet includes applying the flexible sheet over at least a portion of the test article to seal a surface region (such as surface region 24) of the test article from an ambient atmosphere (such as ambient atmosphere 76). The sealed space is formed at least between the flexible sheet and the surface region of the test article. Applying 202 may include forming a flexible enclosure (such as flexible enclosure 12) around the sealed space. Applying 202 may include sealing the flexible sheet to the test article, a base supporting the test article (such as base 26), another flexible sheet, and/or to the original flexible sheet. Applying 202 may include arranging, configuring, and/or forming a frangible zone and/or frangible indicator element in and/or of the flexible sheet and/or a seal of the flexible sheet. The seal may be the seal 16; the frangible indicator element may be the indicator element 112; the frangible zone may be the frangible zone 118. The frangible zone and/or indicator element is configured to break in response to reaction of the indicator gas mixture in the sealed space due to the energy discharge. For example, the frangible zone and/or indicator element may break in response to volume and/or pressure changes in the sealed space due to combustion of the indicator gas mixture in the sealed space.

Filling 204 the sealed space may include flushing the sealed space with the indicator gas mixture. Flushing may include venting the sealed space such that indicator gas mixture may be introduced into the sealed space and cause gas in the sealed space to be displaced by the introduced indicator gas mixture. The displaced gas from the sealed space (which may be the original gas captured in the sealed space or gas introduced into the sealed space) may exit the sealed space, e.g., through a vent of the sealed space. Flushing may include flowing the indicator gas mixture through the sealed space, until prior gases in the sealed space are substantially or completely removed. For example, the total volume of indicator gas mixture flowed through the sealed space may be several times the total volume of the sealed space, e.g., three times or five times the total volume of the sealed space.

Filling 204 may include evacuating the sealed space and/or purging gas from the sealed space and then introducing the indicator gas mixture into the evacuated or purged sealed space. Evacuating the sealed space and/or purging gas from the sealed space may include generating an absolute pressure in the sealed space that is less than 20 kPa, less than 10 kPa, or less than 1 kPa.

Filling 204 may include pressurizing the sealed space with the indicator gas mixture to a suitable test pressure of greater than 50 kPa, greater than 70 kPa, greater than 90 kPa, greater than 100 kPa, greater than 110 kPa, less than 200 kPa, less than 150 kPa, less than 120 kPa, less than 100 kPa, about 90 kPa, about 100 kPa, and/or about 110 kPa. Suitable pressures and other test conditions are described further herein. In particular, filling 204 to a pressure that is less than the pressure of the ambient atmosphere may be beneficial to reduce leakage of indicator gas mixture out of the sealed space and the flexible enclosure. Filling 204 to a pressure that is above the pressure of the ambient atmosphere may be beneficial to reduce contamination of the indicator gas mixture in the sealed space by the ambient atmosphere.

Filling, flowing, flushing, evacuating, and/or purging may be performed with the gas control module 30, the valves 50, the gas mixer 58, the vacuum source 94, etc. as described herein with respect to the test system 10. Filling 204 may include introducing the indicator gas mixture by flowing the indicator gas mixture and/or components thereof from one or more gas sources (such as gas sources 80) into the sealed space. Filling 204 may include using mass flow controllers to regulate the flow of one or more gases into the sealed space.

Methods 200 include applying 206 the energy discharge to the test article while the sealed space includes and/or is filled with the indicator gas mixture. Applying 206 the energy discharge includes applying the energy discharge into, at, and/or to the test article to test whether the discharged energy generates an ignition source (such as ignition source 106) at the test article that is sufficient to react the indicator gas mixture in contact with the test article. Applying 206 the energy discharge may also be referred to as activating the test article, energizing the test article, and/or ignition hazard simulation. The energy discharge may be applied to the test article at a site that is inside the sealed space (i.e., a site on the surface region) or outside of the sealed space (or outside of all sealed spaces as described further herein).

Applying 206 the energy discharge may simulate and/or may be actual operating conditions that the test article may experience such as a lightning strike, a static electrical charge discharge, heat, and/or a spark. Applying 206 the energy discharge may include applying a simulated lightning strike to the test article, applying a voltage across the test article (e.g., a voltage greater than 1 kV (kilovolts) or greater than 5 kV, and generally less than 200 kV), supplying an electrical current through the test article (e.g., a current greater than 1 A (amperes) or greater than 10 A, and generally less than 200,000 A). The energy discharge may have a peak power of greater than 1 kW (kilowatts) or greater than 10 kW, and generally less than 10,000 kW. The energy discharge may be relatively short, for example, having a duration of less than 1 second, less than 0.1 seconds, less than 0.01 seconds, or less than 0.001 seconds, and generally longer than 1 nanosecond. Applying 206 the energy discharge may include heating the test article (e.g., heating a region of the test article), for example, heating to a temperature greater than 200° C., greater than 300° C., or greater than 500° C., and generally less than 2,000° C.

Methods 200 include determining 208 a reaction of the indicator gas mixture in the sealed space in response to the energy discharge. If the indicator gas mixture reacted, then the energy discharge did create an ignition source in the sealed space. If the indicator gas mixture did not react (the indicator gas mixture remains unreacted), then the energy discharge did not create an ignition source of sufficient energy. The reaction of the indicator gas mixture may be combustion or explosive combustion. Determining 208 may include determining the presence, energy, and/or character (e.g., type, duration, etc.) of an ignition source at the surface region in response to the energy discharge.

Determining 208 may include determining the seal integrity of the sealed space and/or the flexible enclosure. Seal integrity may be determined by inspection of the seal and/or the flexible sheet (e.g., determining damage to the seal and/or the flexible sheet). Seal integrity may be determined by verifying 214 the seal integrity, as discussed further herein.

Determining 208 may include arranging an indicator module (such as indicator module 110) in contact with the flexible sheet and/or the indicator gas mixture in the sealed space. The indicator module is configured to change physical state in response to reaction of the indicator gas mixture in the sealed space due to the energy discharge. The physical state may be a position, a conformation, a phase of matter, and/or a chemical composition. Additionally or alternatively, the indicator module may be configured to change the physical state of another element of the flexible enclosure (e.g., rupturing the flexible sheet and/or the seal). The indicator module may be configured to visually indicate reaction of the indicator gas mixture in the sealed space. Determining 208 may include inspecting the indicator module for the physical state change.

Determining 208 may include determining a change in chemical composition of the indicator gas mixture after the energy discharge relative to the before the energy discharge. Determining 208 may include gas analysis, for example sampling a portion of the indicator gas mixture from the sealed space (e.g., via the gas sampling system 96). Determining 208 may include performing techniques such as mass spectrometry, gas chromatography, and/or gas chromatography mass spectrometry. Determining 208 may include performing techniques such as optical spectrometry, optical absorbance, optical transmittance, optical reflectance, nephelometry, luminescence, fluorescence, phosphorescence, laser-induced fluorescence, planar laser-induced fluorescence, laser-excited atomic fluorescence, and/or Fourier transform infrared spectrometry. Determining 208 may include use of a gas analyzer as described herein with respect to the gas sampling system 96.

Methods 200 may include forming 212 the indicator gas mixture prior to and/or during the filling 202. Forming 212 may include mixing components of the indicator gas mixture (e.g., fuel, oxidant, thermally reactive reagent, and/or diluent). Mixing may include mixing in a gas mixer (such as gas mixer 58) that is fluidically coupled to the sealed space. Additionally or alternatively, mixing may include introducing the gas components into the sealed space and then stirring (e.g., with a fan or stirrer) and/or incubating the components in the sealed space until sufficiently mixed.

Methods 200 may include verifying 214 the seal integrity before, during, and/or after filling 204 the sealed space and/or applying 206 the energy discharge. Verifying 214 may be performed by monitoring the pressure in the sealed space before, during, and/or after filling 204 and/or applying 206 the energy discharge. In particular, monitoring may be performed while the sealed space and the flexible enclosure are in a sealed state, with no intentional gas input or gas output, and with all valves, panels, seams, and seals closed.

Verifying 214 may be performed prior to filling 204 to verify that the sealed space and the flexible enclosure are suitably sealed and ready to accept the indicator gas mixture during the filling 204. Verifying 214 may be performed after filling 204 to verify that the sealed space and the flexible enclosure are containing the indicator gas mixture, that the indicator gas mixture is not being significantly diluted by the ambient atmosphere, and that the indicator gas mixture is not being significantly lost to the ambient atmosphere. Verifying 214 may be performed after the applying 206 the energy discharge to verify that the energy discharge did not affect the seal integrity of the sealed space and the flexible enclosure. Additionally or alternatively, determining 208 may include verifying 214 to determine whether the indicator gas mixture reacted and thereby affected the seal integrity, as discussed herein. Verifying 214 may be performed in one or more, or all, of the foregoing sequences.

Verifying 214 the seal integrity may include evacuating the sealed space and determining a leak rate into the sealed space. The evacuation to verify the seal integrity may result in an absolute pressure of less than 20 kPa, less than 10 kPa, or less than 1 kPa. The seal integrity may be considered damaged and/or inadequate if the leak rate is too great (e.g., a leak rate resulting in a pressure change of greater than 1 Pa/min (pascal per minute), greater than 10 Pa/min, or greater than 100 Pa/min into an ambient atmosphere at standard pressure and temperature). The seal integrity may be considered intact if the leak rate is sufficiently low (e.g., less than the limit indicating damage and/or inadequacy). Verifying 214 the seal integrity may include pressurizing the sealed space and determining a leak rate out of the sealed space. The pressurization to verify the seal integrity may result in a relative pressure (or pressure differential) between the sealed space and an ambient atmosphere of greater than 20 kPa, greater than 50 kPa, greater than 100 kPa, less than 500 kPa, less than 200 kPa, and/or less than 100 kPa. The seal integrity may be considered damaged and/or inadequate if the leak rate is too great (e.g., a leak rate resulting in a pressure change of greater than 1 Pa/min, greater than 10 Pa/min, or greater than 100 Pa/min into an ambient atmosphere at standard pressure and temperature). The seal integrity may be considered intact if the leak rate is sufficiently low (e.g., less than the limit indicating damage and/or inadequacy). Pressurization may be performed with suitable gas such as air, inert gas, or the indicator gas mixture.

As an example of verifying 214 before filling 204, methods 200 may include applying 202 the flexible sheet and then verifying 214. Verifying 214 in this example includes evacuating the flexible enclosure formed by the flexible sheet and determining that the leak rate into the sealed space is less than a predetermined vacuum-leak threshold that distinguishes intact seals from damaged and/or inadequate seals. Verifying 214 in this example further includes pressurizing the flexible enclosure formed by the flexible sheet and determining that the leak rate out of the sealed space is less than a predetermined pressure-leak threshold that distinguishes intact seals from damaged and/or inadequate seals. Pressurizing in this example may include pressurizing with air. If the verifying 214 (by evacuation and/or by pressurization) determines that the seal is damaged and/or inadequate, the flexible enclosure may be rebuilt and/or repaired (e.g., by repeating the applying 202 the flexible sheet).

As an example of verifying 214 during and/or after applying 206 the energy discharge, verifying 214 may include monitoring the pressure of the sealed space with a pressure sensor. The pressure sensor may be located in the sealed space or outside of the flexible enclosure. A remotely located pressure sensor may be less affected by the effects of the energy discharge than a proximately located pressure sensor. The pressure sensor may be fluidically coupled to the sealed space.

As an example of determining 208 by verifying 214, methods 200 may include applying 206 the energy discharge and then verifying 214. Verifying 214 in this example includes measuring the leak rate out of the sealed space and determining that the leak rate out of the sealed space is less than the predetermined pressure-leak threshold that distinguishes intact seals from damaged and/or inadequate seals. This step of verifying 214 may be performed with the (potentially reacted) indicator gas mixture in the sealed space after the energy discharge and/or may be performed after also pressurizing the flexible enclosure. Verifying 214 in this example further includes evacuating the flexible enclosure and determining that the leak rate into the sealed space is less than a predetermined vacuum-leak threshold that distinguishes intact seals from damaged and/or inadequate seals.

Methods 200 may include validating that the indicator gas mixture is appropriately mixed and/or that the indicator gas mixture before and/or after the applying 206 the energy discharge is reactive to ignition sources. Validating may include sampling the indicator gas mixture after it is formed and/or sampling the indicator gas mixture in the sealed space. In particular, if the indicator gas mixture is formed by mixing two or more components during and/or after the filling 204, validating may be performed to validate that the indicator gas mixture was mixed appropriately and/or that the expected amounts of the components are present in the indicator gas mixture. Validating may include discharging a controlled ignition source (such as controlled ignition source 124) in contact with the indicator gas mixture in the sealed space or a sample of the indicator gas mixture. Validating with a reliable ignition source (such as the controlled ignition source) validates that components of the corresponding test system function properly. In particular, if applying 206 the energy discharge does not result in an apparent reaction of the indicator gas mixture in the sealed space, the indicator gas mixture in the sealed space after applying 206 the energy discharge may be validated to determine if the indicator gas mixture is reactive. If this validating determines that the indicator gas mixture is not reactive, the method 200 would result in an invalid test.

Methods 200 may include forming more than one sealed space at the surface of the test article. Multiple sealed spaces and/or flexible enclosures may be formed in a similar manner at different sites (different surface regions) on the test article. The sites may be regions to be tested, regions with potential ignition source generators, etc., as discussed with respect to surface regions 24. Methods 200 of incendivity testing of multiple surface regions of a test article may include applying flexible sheets over different portions of the test article to form separate sealed spaces at the surface regions. For each flexible sheet applied, the application may be performed as discussed with respect to applying 202 the flexible sheet. Each of the sealed spaces is filled with an indicator gas mixture. Each sealed space may be filled with the same or different types of indicator gas mixtures. For each sealed space, filling may be performed as discussed with respect to filling 204. Applying 206 the energy discharge may include applying one energy discharge (or group of discharges) to the test article and permitting the energy of the applied energy discharge to distribute to the surface regions of the sealed spaces according to the construction of the test article. Each sealed space does not need to have a separate or dedicated energy discharge to be tested. One energy discharge may be used to potentially generate ignition sources in all of the sealed spaces. After applying the energy discharge, each sealed space, flexible sheet, and/or flexible enclosure may be inspected to determine if an ignition source was generated in the respective sealed space by determining if the indicator gas mixture in the sealed space reacted. For each sealed space, determining if the indicator gas mixture reacted may be performed as discussed with respect to determining 208.

Examples of inventive subject matter according to the present disclosure are described in the following enumerated paragraphs.

A1. An incendivity test method comprising:
applying a flexible sheet over at least a portion of a test article to seal a surface region of the test article from an ambient atmosphere and to form a sealed space between the flexible sheet and the surface region of the test article;
filling the sealed space with an indicator gas mixture;
applying an energy discharge to the test article while the sealed space includes the indicator gas mixture; and
determining whether the indicator gas mixture in the sealed space reacted in response to the energy discharge.

A2. The method of paragraph A1, wherein the indicator gas mixture is a flammable gas mixture.

A2.1. The method of paragraph A2, wherein the flammable gas mixture is formulated to ignite in response to an ignition source at the surface region of the test article, provided that the ignition source has an energy of greater than or equal to a 0.2 mJ electrical arc.

A2.2. The method of any of paragraphs A2-A2.1, wherein the flammable gas mixture includes a fuel and an oxidant.

A2.2.1. The method of paragraph A2.2, wherein the fuel is at least one of gaseous, vaporous, and an aerosol.

A2.2.2. The method of any of paragraphs A2.2-A2.2.1, wherein the fuel is a combustion fuel, optionally selected from the group consisting of a hydrocarbon fuel, molecular hydrogen, methane, propane, gasoline, kerosene, and ethylene.

A2.2.3. The method of any of paragraphs A2.2-A2.2.2, wherein the oxidant is at least one of gaseous, vaporous, and an aerosol.

A2.2.4. The method of any of paragraphs A2.2-A2.2.3, wherein the oxidant is selected from the group consisting of molecular oxygen, nitrous oxide, and hydrogen peroxide.

A2.3. The method of any of paragraphs A2-A2.2.4, wherein the flammable gas mixture includes a diluent that includes one or more species selected from the group consisting of an inert gas, nitrogen, argon, and helium.

A3. The method of paragraph A1, wherein the indicator gas mixture is a non-flammable gas mixture.

A3.1. The method of paragraph A3, wherein the non-flammable gas mixture is formulated to react in response to an ignition source at the surface region, provided that the ignition source has an energy of greater than or equal to a 0.2 mJ electrical arc, and optionally wherein the non-flammable gas mixture is formulated to react non-explosively to the ignition source.

A3.2. The method of any of paragraphs A3-A3.1, wherein the non-flammable gas mixture includes a thermally reactive reagent.

A3.2.1. The method of paragraph A3.2, wherein the thermally reactive reagent includes, optionally is, at least one of a thermally reactive gas and a thermally reactive aerosol.

A3.2.2. The method of any of paragraphs A3.2-A3.2.1, wherein the non-flammable gas mixture is a mixture that is too lean to support self-propagating combustion of the thermally reactive reagent.

A3.2.3. The method of any of paragraphs A3.2-A3.2.2, wherein the non-flammable gas mixture has a concentration of the thermally reactive reagent that is below a lean ignition limit.

A3.2.4. The method of any of paragraphs A3.2-A3.2.3, wherein the thermally reactive reagent is a combustion fuel, optionally selected from the group consisting of a hydrocarbon fuel, a flammable gas, molecular hydrogen, methane, propane, gasoline, kerosene, and ethylene.

A3.2.5. The method of any of paragraphs A3.2-A3.2.4, wherein the thermally reactive reagent is configured to thermally decompose.

A3.2.6. The method of any of paragraphs A3.2-A3.2.5, wherein the thermally reactive reagent is a halocarbon, optionally selected from the group consisting of an alkyl halide, a chlorocarbon, a fluorocarbon, a bromocarbon, a chlorofluorocarbon, chloroethane, and methyl bromide.

A3.3. The method of any of paragraphs A3-A3.2.6, wherein the non-flammable gas mixture includes an oxidant, optionally selected from the group consisting of molecular oxygen, nitrous oxide, and hydrogen peroxide.

A3.4. The method of any of paragraphs A3-A3.3, wherein the non-flammable gas mixture includes a diluent that includes one or more species selected from the group consisting of an inert gas, nitrogen, argon, and helium, and optionally wherein the diluent is configured not to react with a/the thermally reactive reagent.

A4. The method of any of paragraphs A1-A3.4, wherein the applying the flexible sheet includes forming a flexible enclosure around the sealed space.

A5. The method of any of paragraphs A1-A4, wherein the applying the flexible sheet includes sealing the flexible sheet to at least one of the test article, a base supporting the test article, and another flexible sheet.

A6. The method of any of paragraphs A1-A5, wherein the applying the flexible sheet includes sealing the flexible sheet to itself.

A7. The method of any of paragraphs A1-A6, wherein the applying the flexible sheet includes configuring at least one of the flexible sheet and a seal of the flexible sheet to break in response to reaction of the indicator gas mixture in the sealed space due to the energy discharge.

A8. The method of any of paragraphs A1-A7, wherein at least one of the flexible sheet and a seal of the flexible sheet is configured to break in response to reaction of the indicator gas mixture in the sealed space due to the energy discharge.

A9. The method of any of paragraphs A1-A8, wherein the flexible sheet is one of elastic and inelastic.

A10. The method of any of paragraphs A1-A9, wherein the flexible sheet is gas impermeant, and optionally has an oxygen transmission rate of less than 10 $mL/m^2/day$ at standard pressure and temperature.

A11. The method of any of paragraphs A1-A10, wherein the flexible sheet has a thickness of less than 1 mm, less than 0.5 mm, less than 0.2 mm, less than 0.02 mm, greater than 0.001 mm, and/or greater than 0.01 mm.

A12. The method of any of paragraphs A1-A11, wherein the flexible sheet is a sheet that includes one or more layers that each independently includes, optionally is composed of, plastic, metalized plastic film, polyester, polyethylene, polypropylene, polyethylene terephthalate, biaxially-oriented polyethylene terephthalate, polyamide, polyimide, rubber, synthetic rubber, polyurethane, polymers of isoprene, polymers of butadiene, and polymers of styrene.

A13. The method of any of paragraphs A1-A12, wherein the flexible sheet is a first flexible sheet, the surface region is a first surface region, and the sealed space is a first sealed space, and wherein the method further comprises:

applying a second flexible sheet over a portion of the test article to seal a second surface region of the test article from the ambient atmosphere and to form a second sealed space between the second flexible sheet and the second surface region of the test article; and filling the second sealed space with the indicator gas mixture;

wherein the applying the energy discharge includes applying the energy discharge to the test article while the first sealed space and the second sealed space include the indicator gas mixture; and determining whether the indicator gas mixture in the second sealed space reacted in response to the energy discharge.

A13.1. The method of paragraph A13, wherein the determining with respect to the first sealed space includes determining a presence of a first ignition source at the first surface region in response to the energy discharge.

A13.2. The method of any of paragraphs A13-A13.1, wherein the determining with respect to the second sealed space includes determining a presence of a second ignition source at the second surface region in response to the energy discharge.

A13.3. The method of any of paragraphs A13-A13.2, further comprising masking the test article outside of the first surface region and the second surface region to suppress ignition source formation outside of the first surface region and the second surface region.

A14. The method of any of paragraphs A1-A13.3, further comprising masking the test article outside of the surface region to suppress ignition source formation outside of the surface region.

A15. The method of any of paragraphs A1-A14, wherein the filling includes flushing the sealed space with the indicator gas mixture.

A16. The method of any of paragraphs A1-A15, wherein the filling includes pressurizing the sealed space with the indicator gas mixture to a pressure of at least one of greater than 50 kPa, greater than 70 kPa, greater than 90 kPa, greater than 100 kPa, greater than 110 kPa, less than 200 kPa, less than 150 kPa, less than 120 kPa, less than 100 kPa, about 90 kPa, about 100 kPa, and about 110 kPa.

A17. The method of any of paragraphs A1-A16, further comprising evacuating the sealed space prior to the filling.

A18. The method of any of paragraphs A1-A17, wherein the applying the energy discharge includes applying the energy discharge while the sealed space is filled with the indicator gas mixture.

A19. The method of any of paragraphs A1-A18, wherein the applying the energy discharge includes creating an ignition source at the surface region of the test article A19.1. The method of paragraph A19, wherein the ignition source discharges an energy of less than 10 mJ, less than 1 mJ, greater than 0.1 mJ, and/or greater than 0.2 mJ.

A19.2. The method of any of paragraphs A19-A19.1, wherein the ignition source discharges an energy equivalent to an electrical arc having an energy of less than 10 mJ, less than 1 mJ, greater than 0.1 mJ, and/or greater than 0.2 mJ.

A19.3. The method of any of paragraphs A19-A19.2, wherein the ignition source includes, optionally is, at least one of an electrical arc, a spark, a hot surface, a hot particle ejection, an electrostatic discharge, and a flame.

A20. The method of any of paragraphs A1-A19.3, wherein the applying the energy discharge includes applying a simulated lightning strike to the test article.

A21. The method of any of paragraphs A1-A20, wherein the applying the energy discharge includes applying a voltage across the test article, and optionally wherein the voltage is greater than 1 kV or greater than 5 kV.

A22. The method of any of paragraphs A1-A21, wherein the applying the energy discharge includes supplying a current through the test article, and optionally wherein the current is greater than 1 A or greater than 10 A.

A23. The method of any of paragraphs A1-A22, wherein the energy discharge has a peak power of greater than 1 kW or greater than 10 kW.

A24. The method of any of paragraphs A1-A23, wherein the applying the energy discharge includes heating the test article.

A25. The method of any of paragraphs A1-A24, wherein the applying the energy discharge includes applying the energy discharge at a position on the test article that is outside of the sealed space and/or that is at an application site spaced apart from the sealed space.

A26. The method of any of paragraphs A1-A24, wherein the applying the energy discharge includes applying the energy discharge to the surface region of the test article.

A27. The method of any of paragraphs A1-A26, wherein the determining includes determining a presence of an ignition source at the surface region in response to the energy discharge.

A28. The method of any of paragraphs A1-A27, wherein the determining includes determining whether the indicator gas mixture in the sealed space ignited and/or combusted in response to the energy discharge.

A29. The method of any of paragraphs A1-A28, wherein the determining includes determining a seal integrity of the sealed space.

A29.1. The method of paragraph A29, wherein the determining the seal integrity includes evacuating the sealed space and determining a leak rate into the sealed space.

A29.2. The method of any of paragraphs A29-A29.1, wherein the determining the seal integrity includes pressurizing the sealed space and determining a leak rate out of the sealed space.

A30. The method of any of paragraphs A1-A29.2, wherein the determining includes arranging an indicator module in contact with at least one of the flexible sheet and the indicator gas mixture in the sealed space, wherein the indicator module is configured to change physical state in response to reaction of the indicator gas mixture in the sealed space due to the energy discharge.

A30.1. The method of paragraph A30, wherein the physical state is at least one of a position, a conformation, a phase of matter, and a chemical composition.

A30.2. The method of any of paragraphs A30-A30.1, wherein the indicator module is configured to visually indicate reaction of the indicator gas mixture in the sealed space.

A30.3. The method of any of paragraphs A30-A30.2, wherein the indicator module includes a frangible element that is configured to break in response to reaction of the indicator gas mixture in the sealed space.

A30.4. The method of any of paragraphs A30-A30.3, wherein the indicator module includes a deformable element that is configured to plastically deform in response to reaction of the indicator gas mixture in the sealed space.

A30.5. The method of any of paragraphs A30-A30.4, wherein the indicator module includes a displaceable element that is configured to stably displace in response to reaction of the indicator gas mixture in the sealed space.

A30.6. The method of any of paragraphs A30-A30.5, wherein the indicator module includes a piercing element that is configured to rupture the flexible sheet in response to reaction of the indicator gas mixture in the sealed space.

A30.7. The method of any of paragraphs A30-A30.6, wherein the indicator module includes a phase-change element that is configured change from a solid to at least one of a liquid and a gas in response to reaction of the indicator gas mixture in the sealed space.

A31. The method of any of paragraphs A1-A30.7, wherein the determining includes determining a change in chemical composition of the indicator gas mixture after the energy discharge relative to before the energy discharge.

A31.1. The method of paragraph A31, wherein the determining the change in chemical composition is by a gas analysis technique selected from the group consisting of mass spectrometry, gas chromatography, and gas chromatography mass spectrometry.

A31.2. The method of any of paragraphs A31-A31.1, wherein the determining the change in chemical composition is by an optical technique selected from the group consisting of optical spectrometry, optical absorbance, optical transmittance, optical reflectance, nephelometry, luminescence, fluorescence, phosphorescence, laser-induced fluorescence, planar laser-induced fluorescence, laser-excited atomic fluorescence, and Fourier transform infrared spectrometry.

A32. The method of any of paragraphs A1-A31.2, further comprising forming the indicator gas mixture while filling the sealed space with the indicator gas mixture.

A32.1. The method of paragraph A32, wherein the forming includes mixing a first gas that includes an oxidant and a second gas that includes a fuel.

A32.1.1. The method of paragraph A32.1, wherein the mixing includes mixing the first gas and the second gas in a gas mixer fluidically coupled to the sealed space.

A32.1.2. The method of any of paragraphs A32.1-A32.1.1, wherein the first gas is an oxidant mixture gas, optionally air.

A32.1.3. The method of any of paragraphs A32.1-A32.1.2, wherein the second gas is one of a fuel mixture gas and a fuel gas.

A33. The method of any of paragraphs A1-A32.1.3, further comprising verifying a seal integrity of the sealed space prior to applying the energy discharge.

A33.1. The method of paragraph A33, wherein the verifying the seal integrity includes evacuating the sealed space and determining a leak rate into the sealed space of less than a predetermined vacuum-leak threshold.

A33.2. The method of any of paragraphs A33-A33.1, wherein the verifying the seal integrity includes pressurizing the sealed space and determining a leak rate out of the sealed space of less than a predetermined pressure-leak threshold.

A34. The method of any of paragraphs A1-A33.2, further comprising validating that the indicator gas mixture reacts to ignition source events by discharging a controlled ignition source in a sample of the indicator gas mixture from the sealed space.

A34.1. The method of paragraph A34, wherein the validating is performed before applying the energy discharge.

A34.2. The method of any of paragraphs A34-A34.1, wherein the validating includes extracting the sample of the indicator gas mixture from the sealed space before applying the energy discharge.

A34.3. The method of any of paragraphs A34-A34.2, wherein the validating the indicator gas mixture includes discharging the controlled ignition source within the sealed space with the test article after the applying the energy discharge.

A34.4. The method of any of paragraphs A34-A34.3, wherein the discharging the controlled ignition source discharges an energy of less than 1 mJ, less than 0.5 mJ, greater than 0.01 mJ, greater than 0.1 mJ, and/or about 0.2 mJ.

A34.5. The method of any of paragraphs A34-A34.4, wherein the controlled ignition source produces, optionally is, at least one of an electrical arc, a spark, a hot surface, a hot particle ejection, an electrostatic discharge, and a flame.

A35. The method of any of paragraphs A1-A34.5, wherein the ambient atmosphere includes, optionally is, at least one of air, molecular oxygen, a flammable gas, an inert gas, nitrogen, and argon.

A36. The method of any of paragraphs A1-A35, wherein the test article is a solid form and optionally includes one or more of metal, aluminum, plastic, and fiber-reinforced composite material.

A37. The method of any of paragraphs A1-A36, wherein the test article is an aerospace component, and optionally at least one of an aircraft, a wing, a fuselage, an empennage, an aircraft skin, an aircraft frame, a fuel system, a fuel tank, a fuel pump, and an electrical enclosure.

B1. A test system, optionally an aerospace component test system, comprising:
a test article;
a flexible enclosure that includes a flexible sheet sealed over at least a portion of the test article to seal a surface region of the test article from an ambient atmosphere and to form a sealed space between the flexible sheet and the surface region of the test article;
an indicator gas mixture in the sealed space, wherein the indicator gas mixture is formulated to react to an ignition source generated at the surface region of the test article; and
an energy source configured to apply an energy discharge to the test article.

B2. The test system of paragraph B1, wherein the indicator gas mixture is a flammable gas mixture.

B2.1. The test system of paragraph B2, wherein the flammable gas mixture is formulated to ignite in response to an ignition source at the surface region of the test article, provided that the ignition source has an energy of greater than or equal to a 0.2 mJ electrical arc.

B2.2. The test system of any of paragraphs B2-B2.1, wherein the flammable gas mixture includes a fuel and an oxidant.

B2.2.1. The test system of paragraph B2.2, wherein the fuel is at least one of gaseous, vaporous, and an aerosol.

B2.2.2. The test system of any of paragraphs B2.2-B2.2.1, wherein the fuel is a combustion fuel, optionally selected from the group consisting of a hydrocarbon fuel, molecular hydrogen, methane, propane, gasoline, kerosene, and ethylene.

B2.2.3. The test system of any of paragraphs B2.2-B2.2.2, wherein the oxidant is at least one of gaseous, vaporous, and an aerosol.

B2.2.4. The test system of any of paragraphs B2.2-B2.2.3, wherein the oxidant is selected from the group consisting of molecular oxygen, nitrous oxide, and hydrogen peroxide.

B2.3. The test system of any of paragraphs B2-B2.2.4, wherein the flammable gas mixture includes a diluent that includes one or more species selected from the group consisting of an inert gas, nitrogen, argon, and helium.

B3. The test system of paragraph B1, wherein the indicator gas mixture is a non-flammable gas mixture.

B3.1. The test system of paragraph B3, wherein the non-flammable gas mixture is formulated to react in response to an ignition source at the surface region, provided that the ignition source has an energy of greater than or equal to a 0.2 mJ electrical arc, and optionally wherein the non-flammable gas mixture is formulated to react non-explosively to the ignition source.

B3.2. The test system of any of paragraphs B3-B3.1, wherein the non-flammable gas mixture includes a thermally reactive reagent.

B3.2.1. The test system of paragraph B3.2, wherein the thermally reactive reagent includes, optionally is, at least one of a thermally reactive gas and a thermally reactive aerosol.

B3.2.2. The test system of any of paragraphs B3.2-B3.2.1, wherein the non-flammable gas mixture is a mixture that is too lean to support self-propagating combustion of the thermally reactive reagent.

B3.2.3. The test system of any of paragraphs B3.2-B3.2.2, wherein the non-flammable gas mixture has a concentration of the thermally reactive reagent that is below a lean ignition limit.

B3.2.4. The test system of any of paragraphs B3.2-B3.2.3, wherein the thermally reactive reagent is a combustion fuel, optionally selected from the group consisting of a hydrocarbon fuel, a flammable gas, molecular hydrogen, methane, propane, gasoline, kerosene, and ethylene.

B3.2.5. The test system of any of paragraphs B3.2-B3.2.4, wherein the thermally reactive reagent is configured to thermally decompose.

B3.2.6. The test system of any of paragraphs B3.2-B3.2.5, wherein the thermally reactive reagent is a halocarbon, optionally selected from the group consisting of an alkyl halide, a chlorocarbon, a fluorocarbon, a bromocarbon, a chlorofluorocarbon, chloroethane, and methyl bromide.

B3.3. The test system of any of paragraphs B3-B3.2.6, wherein the non-flammable gas mixture includes an oxidant, optionally selected from the group consisting of molecular oxygen, nitrous oxide, and hydrogen peroxide.

B3.4. The test system of any of paragraphs B3-B3.3, wherein the non-flammable gas mixture includes a diluent that includes one or more species selected from the group consisting of an inert gas, nitrogen, argon, and helium, and optionally wherein the diluent is configured not to react with a/the thermally reactive reagent.

B4. The test system of any of paragraphs B1-B3.4, wherein the flexible sheet is sealed to at least one of the test article, a base supporting the test article, and another flexible sheet, and optionally wherein the test system includes the base.

B5. The test system of any of paragraphs B1-B4, wherein the flexible sheet is sealed to itself.

B6. The test system of any of paragraphs B1-B5, wherein the flexible sheet is one of elastic and inelastic.

B7. The test system of any of paragraphs B1-B6, wherein the flexible sheet is gas impermeant, and optionally has an oxygen transmission rate of less than 10 mL/m$^2$/day at standard pressure and temperature.

B8. The test system of any of paragraphs B1-B7, wherein the flexible sheet has a thickness of less than 1 mm, less than 0.5 mm, less than 0.2 mm, less than 0.02 mm, greater than 0.001 mm, and/or greater than 0.01 mm.

B9. The test system of any of paragraphs B1-B8, wherein the flexible sheet is a sheet that includes one or more layers that each independently includes, optionally is composed of, plastic, metalized plastic film, polyester, polyethylene, polypropylene, polyethylene terephthalate, biaxially-oriented polyethylene terephthalate, polyamide, polyimide, rubber, synthetic rubber, polyurethane, polymers of isoprene, polymers of butadiene, and polymers of styrene.

B10. The test system of any of paragraphs B1-B9, wherein the test system includes a plurality of flexible enclosures, wherein each flexible enclosure includes a flexible sheet sealed over a portion of the test article to seal a surface region of the test article from an ambient atmosphere and from other flexible enclosures, wherein each flexible enclosure encloses a sealed space between the flexible sheet of the flexible enclosure and the surface region of the test article, and wherein the indicator gas mixture is in the sealed space of each of the flexible enclosures.

B11. The test system of any of paragraphs B1-1310, wherein at least one of the flexible sheet and a seal of the flexible sheet is configured to break in response to reaction of the indicator gas mixture in the sealed space due to the energy discharge.

B12. The test system of any of paragraphs B1-B11, wherein the flexible enclosure includes a gas control module with one or more gas ports that is configured to at least one of fill, flush, purge, and sample gas in the sealed space of the flexible enclosure.

B12.1. The test system of paragraph B12, wherein at least one of the gas ports is configured to introduce the indicator gas mixture into the sealed space B12.2. The test system of any of paragraphs B12-B12.1, wherein the gas control module includes one or more valves to control gas flow through at least one of the gas ports.

B12.2.1. The test system of paragraph B12.2, wherein each of the gas ports is associated with at least one of the valves that is configured to control gas flow through the respective gas port.

B12.2.2. The test system of any of paragraphs B12.2-B12.2.1, wherein at least one of the valves includes at least one of a stop valve, a check valve, and a pressure relief valve.

B12.3. The test system of any of paragraphs B12-B12.2.2, wherein the gas control module includes an oxidant port configured to introduce a gas that includes oxidant into the sealed space.

B12.3.1. The test system of paragraph B12.3, wherein the gas control module includes a check valve arranged to prevent leakage from the sealed space through the oxidant port when no gas is flowing through the oxidant port into the sealed space from outside the sealed space.

B12.4. The test system of any of paragraphs B12-B12.3.1, wherein the gas control module includes a fuel port configured to introduce a gas that includes fuel into the sealed space.

B12.4.1. The test system of paragraph B12.4, wherein the gas control module includes a check valve arranged to prevent leakage from the sealed space through the fuel port when no gas is flowing through the fuel port into the sealed space from outside the sealed space.

B12.4.2. The test system of any of paragraphs B12.4-B12.4.1, when also depending from paragraph B12.3, wherein the gas control module includes a gas mixer configured to mix oxidant from the oxidant port and fuel from the fuel port to form the indicator gas mixture and to introduce the indicator gas mixture into the sealed space, and optionally wherein the gas control module includes a first check valve arranged to prevent leakage from the sealed space through the gas mixer and the oxidant port when no gas is flowing through the oxidant port into the gas mixer and the gas control module includes a second check valve arranged to prevent leakage from the sealed space through the gas mixer and the fuel port when no gas is flowing through the fuel port into the gas mixer.

B12.5. The test system of any of paragraphs B12-612.4.2, wherein the gas control module includes a relief port configured to release gas from the sealed space when pressure within the sealed space is greater than a predetermined threshold, and optionally wherein the gas control module includes a pressure relief valve arranged to release gas from the sealed space through the relief port when pressure within the sealed space is greater than the predetermined threshold.

B12.6. The test system of any of paragraphs B12-B12.5, wherein the gas control module includes a vacuum port configured to at least one of evacuate and vent the sealed space, and optionally wherein the gas control module includes a stop valve configured to selectively isolate the sealed space from the vacuum port.

B12.7. The test system of any of paragraphs B12-B12.6, wherein the gas control module includes a sample port configured to extract a sample of gas from the sealed space, and optionally wherein the gas control module includes a stop valve configured to selectively isolate the sealed space from the sample port.

B13. The test system of any of paragraphs B1-B12.7, further comprising a gas source configured to supply the indicator gas mixture to the flexible enclosure and optionally wherein the gas source is connected to the flexible enclosure via a gas port of the flexible enclosure and a valve that is configured to control a flow of the indicator gas mixture from the gas source to the sealed space of the flexible enclosure.

B14. The test system of any of paragraphs B1-B13, further comprising a gas mixer, a fuel source configured to supply a first gas including fuel to the gas mixer, and an oxidant source configured to supply a second gas including oxidant to the gas mixer, wherein the gas mixer is configured to mix the first gas and the second gas to form the indicator gas mixture and to supply the sealed space of the flexible enclosure with the indicator gas mixture.

B15. The test system of any of paragraphs B1-B14, further comprising a vacuum source configured to evacuate the sealed space of the flexible enclosure.

B16. The test system of any of paragraphs B1-B15, further comprising a gas sampling system configured to extract a sample of the indicator gas mixture from the sealed space.

B16.1. The test system of paragraph B16, wherein the gas sampling system is configured to determine at least one of a flammability and a chemical composition of the sample of the indicator gas mixture.

B16.2. The test system of any of paragraphs B16-B16.1, wherein the gas sampling system includes a gas analyzer that includes, optionally is, at least one of a mass spectrometer, a gas chromatography apparatus, a gas chromatography mass spectrometer, and an optical spectrometer.

B16.3. The test system of any of paragraphs B16-B16.2, wherein the gas sampling system includes a controlled ignition source configured to deliver a controlled-energy discharge into the sample of the indicator gas mixture.

B16.3.1. The test system of paragraph B16.3, wherein the controlled ignition source is configured to discharge an energy of less than 1 mJ, less than 0.5 mJ, greater than 0.01 mJ, greater than 0.1 mJ, and/or about 0.2 mJ.

B16.3.2. The test system of any of paragraphs B16.3-616.3.1, wherein the controlled ignition source is configured to discharge an energy equivalent to an electrical arc having an energy of less than 10 mJ, less than 1 mJ, greater than 0.1 mJ, and/or greater than 0.2 mJ.

B16.3.3. The test system of any of paragraphs B16.3-616.3.2, wherein the controlled ignition source is configured to produce at least one of an electrical arc, a spark, a hot surface, a hot particle ejection, an electrostatic discharge, and a flame.

B17. The test system of any of paragraphs B1-616.3.3, further comprising a controlled ignition source configured to deliver a controlled-energy discharge into the sealed space.

B17.1. The test system of paragraph B17, wherein the controlled ignition source is configured to discharge an energy of less than 1 mJ, less than 0.5 mJ, greater than 0.01 mJ, greater than 0.1 mJ, and/or about 0.2 mJ.

B17.2. The test system of any of paragraphs B17-B17.1, wherein the controlled ignition source is configured to discharge an energy equivalent to an electrical arc having an energy of less than 1 mJ, less than 0.5 mJ, greater than 0.01 mJ, greater than 0.1 mJ, and/or about 0.2 mJ.

B17.3. The test system of any of paragraphs B17-B17.2, wherein the controlled ignition source is configured to produce at least one of an electrical arc, a spark, a hot surface, a hot particle ejection, an electrostatic discharge, and a flame.

B18. The test system of any of paragraphs B1-B17.3, further comprising an indicator module in contact with at least one of the flexible sheet and the indicator gas mixture in the sealed space, wherein the indicator module is configured to change physical state in response to reaction of the indicator gas mixture in the sealed space due to the energy discharge.

B18.1. The test system of paragraph B18, wherein the physical state is at least one of a position, a conformation, a phase of matter, and a chemical composition.

B18.2. The test system of any of paragraphs B18-B18.1, wherein the indicator module is configured to visually indicate reaction of the indicator gas mixture in the sealed space.

B18.3. The test system of any of paragraphs B18-B18.2, wherein the indicator module includes a frangible element that is configured to break in response to reaction of the indicator gas mixture in the sealed space.

B18.4. The test system of any of paragraphs B18-B18.3, wherein the indicator module includes a deformable element that is configured to plastically deform in response to reaction of the indicator gas mixture in the sealed space.

B18.5. The test system of any of paragraphs B18-B18.4, wherein the indicator module includes a displaceable element that is configured to stably displace in response to reaction of the indicator gas mixture in the sealed space.

B18.6. The test system of any of paragraphs B18-B18.5, wherein the indicator module includes a piercing element that is configured to rupture the flexible sheet in response to reaction of the indicator gas mixture in the sealed space.

B18.7. The test system of any of paragraphs B18-B18.6, wherein the indicator module includes a phase-change element that is configured change from a solid to at least one of a liquid and a gas in response to reaction of the indicator gas mixture in the sealed space.

B19. The test system of any of paragraphs B1-B18.7, wherein the energy source is at least one of a lightning strike simulator, an electrical power source, an electrical voltage source, and an electrical current source.

B20. The test system of any of paragraphs B1-B19, wherein the energy source is arranged to apply the energy discharge to the test article at an application site that is one of outside of the surface region of the test article and inside the surface region of the test article.

B21. The test system of any of paragraphs B1-B20, further comprising a controller configured to discharge the energy source to apply the energy discharge to the test article and configured to fill the sealed space with the indicator gas mixture, and optionally wherein the controller is programmed to perform the method of any of paragraphs A1-A37.

B22. The test system of any of paragraphs B1-B21, wherein the ambient atmosphere includes, optionally is, at least one of air, molecular oxygen, a flammable gas, an inert gas, nitrogen, and argon.

B23. The test system of any of paragraphs B1-B22, wherein the test article is a solid form and optionally includes one or more of metal, aluminum, plastic, and fiber-reinforced composite material.

B24. The test system of any of paragraphs B1-B23, wherein the test article is an aerospace component, and optionally at least one of an aircraft, a wing, a fuselage, an empennage, an aircraft skin, an aircraft frame, a fuel system, a fuel tank, a fuel pump, and an electrical enclosure.

B25. The use of the test system of any of paragraphs B1-B24 to test a response of the test article to the energy discharge.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, prepared, formed, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa. Similarly, subject matter that is recited as being configured to perform a particular function may additionally or alternatively be described as being operative to perform that function.

As used herein, the phrase, "for example," the phrase, "as an example," and/or simply the term "example," when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

As used herein, the phrases "at least one of" and "one or more of," in reference to a list of more than one entity, means any one or more of the entities in the list of entities, and is not limited to at least one of each and every entity specifically listed within the list of entities. For example, "at least one of A and B" (or, equivalently, "at least one of A or B," or, equivalently, "at least one of A and/or B") may refer to A alone, B alone, or the combination of A and B.

As used herein, the singular forms "a", "an" and "the" may be intended to include the plural forms as well, unless the context clearly indicates otherwise.

The various disclosed elements of systems and steps of methods disclosed herein are not required of all systems and methods according to the present disclosure, and the present disclosure includes all novel and non-obvious combinations and subcombinations of the various elements and steps disclosed herein. Moreover, any of the various elements and steps, or any combination of the various elements and/or steps, disclosed herein may define independent inventive subject matter that is separate and apart from the whole of a disclosed system or method. Accordingly, such inventive subject matter is not required to be associated with the specific systems and methods that are expressly disclosed herein, and such inventive subject matter may find utility in systems and/or methods that are not expressly disclosed herein.

The invention claimed is:

1. An incendivity test method comprising:
applying a flexible sheet over a portion of a test article to fluidically isolate a surface region of the test article from an ambient atmosphere and to form a sealed space between the flexible sheet and the surface region of the test article, wherein the flexible sheet is composed of a flexible material and is configured to at least partially conform to the test article when applied to the test article, and wherein the surface region is less than an entirety of an outer surface of the test article;
filling the sealed space with an indicator gas mixture;
applying an energy discharge to the test article while the sealed space includes the indicator gas mixture; and
determining whether the indicator gas mixture in the sealed space reacted in response to the energy discharge.

2. The method of claim 1, wherein the applying the flexible sheet includes sealing the flexible sheet to at least one of the test article, a base supporting the test article, and another flexible sheet.

3. The method of claim 1, wherein the applying the flexible sheet includes configuring at least one of the flexible sheet and a seal of the flexible sheet to break in response to reaction of the indicator gas mixture in the sealed space due to the energy discharge.

4. The method of claim 1, wherein the flexible sheet is a first flexible sheet, the surface region is a first surface region, and the sealed space is a first sealed space, and wherein the method further comprises:
applying a second flexible sheet over a portion of the test article to fluidically isolate a second surface region of the test article from the ambient atmosphere and to form a second sealed space between the second flexible sheet and the second surface region of the test article, wherein the second surface region is less than the entirety of the outer surface of the test article; and
filling the second sealed space with the indicator gas mixture;
wherein the applying the energy discharge includes applying the energy discharge to the test article while the first sealed space and the second sealed space include the indicator gas mixture; and
determining whether the indicator gas mixture in the second sealed space reacted in response to the energy discharge.

5. The method of claim 4, further comprising masking the test article outside of the first surface region and the second surface region to suppress ignition source formation outside of the first surface region and the second surface region.

6. The method of claim 4, wherein the applying the energy discharge includes applying the energy discharge at a position on the test article that is outside of the first sealed space and the second sealed space.

7. The method of claim 1, further comprising evacuating the sealed space prior to the filling.

8. The method of claim 1, wherein the determining includes arranging an indicator module in contact with at least one of the flexible sheet and the indicator gas mixture in the sealed space, wherein the indicator module is configured to change physical state in response to reaction of the indicator gas mixture in the sealed space due to the energy discharge.

9. The method of claim 8, wherein the indicator module includes a frangible element that is configured to break in response to reaction of the indicator gas mixture in the sealed space.

10. The method of claim 8, wherein the indicator module includes a displaceable element that is configured to stably displace in response to reaction of the indicator gas mixture in the sealed space.

11. An incendivity test method comprising:
applying a flexible sheet over a portion of a test article to fluidically isolate a surface region of the test article from an ambient atmosphere and to form a sealed space between the flexible sheet and the surface region of the test article, wherein the flexible sheet is composed of a flexible material and is configured to at least partially conform to the test article when applied to the test article, and wherein the surface region is less than an entirety of an outer surface of the test article;

filling the sealed space with a flammable gas mixture;

applying an energy discharge to the test article while the sealed space is filled with the flammable gas mixture; and determining whether the flammable gas mixture in the sealed space reacted in response to the energy discharge.

12. The method of claim 11, wherein the determining includes determining whether the flammable gas mixture in the sealed space ignited in response to the energy discharge.

13. The method of claim 11, wherein the applying the energy discharge includes applying the energy discharge at a position on the test article that is outside of the sealed space.

14. The method of claim 11, further comprising masking the test article outside of the surface region to suppress ignition source formation outside of the surface region.

15. The method of claim 11, wherein the determining includes determining a seal integrity of the sealed space.

16. The method of claim 11, further comprising forming the flammable gas mixture while filling the sealed space with the flammable gas mixture.

17. The method of claim 16, wherein the forming includes mixing a gas that includes an oxidant and a fuel gas.

18. A test system, comprising:

a test article;

a flexible enclosure that includes a flexible sheet sealed over a portion of the test article to fluidically isolate a surface region of the test article from an ambient atmosphere and to form a sealed space between the flexible sheet and the surface region of the test article, wherein the surface region is less than an entirety of an outer surface of the test article, wherein the flexible sheet is composed of a flexible material and is configured to at least partially conform to the test article when applied to the test article, and wherein the flexible enclosure includes a gas control module that is configured to fill, flush and purge gas in the sealed space of the flexible enclosure;

a flammable gas mixture in the sealed space, wherein the flammable gas mixture is formulated to react to an ignition source generated at the surface region of the test article, provided that the ignition source has an energy of greater than or equal to a 0.2 mJ electrical arc; and an energy source configured to apply an energy discharge to the test article.

19. The test system of claim 18, wherein the test system includes a plurality of flexible enclosures, wherein each flexible enclosure includes a flexible sheet sealed over a portion of the test article to fluidically isolate a surface region of the test article from an ambient atmosphere and from other flexible enclosures, wherein each flexible enclosure encloses a sealed space between the flexible sheet of the flexible enclosure and the surface region of the test article, and wherein the flammable gas mixture is in the sealed space of each of the flexible enclosures.

20. The test system of claim 18, wherein the gas control module includes (a) an oxidant port configured to introduce a gas that includes oxidant into the sealed space, (b) a fuel port configured to introduce a gas that includes fuel into the sealed space, (c) a gas mixer configured to mix oxidant from the oxidant port and fuel from the fuel port to form the flammable gas mixture and to introduce the flammable gas mixture into the sealed space, and (d) a vacuum port configured to at least one of evacuate and vent the sealed space.

21. The system of claim 18, wherein the test article is an aerospace component.

22. The method of claim 1, wherein the test article is an aerospace component.

23. The method of claim 11, wherein the test article is an aerospace component.

24. The method of claim 11, wherein the applying the energy discharge results in an ignition source at the surface region of the test article having an energy of greater than or equal to a 0.2 mJ electrical arc, and wherein the flammable gas mixture is formulated to react to the ignition source.

25. The method of claim 22, wherein the aerospace component is one of an aircraft, a wing, a fuselage, an empennage, an aircraft skin, an aircraft frame, a fuel system, a fuel tank, a fuel pump, and an electrical enclosure.

26. The method of claim 23, wherein the aerospace component is one of an aircraft, a wing, a fuselage, an empennage, an aircraft skin, an aircraft frame, a fuel system, a fuel tank, a fuel pump, and an electrical enclosure.

* * * * *